(12) United States Patent
Eckhardt et al.

(10) Patent No.: US 7,495,003 B2
(45) Date of Patent: Feb. 24, 2009

(54) 8-(3-AMINO-PIPERIDIN-1-YL)-7-(BUT-2-YNYL)-XANTHINES, THE PREPARATION THEREOF AND THEIR USE AS PHARMACEUTICAL COMPOSITIONS

(75) Inventors: Matthias Eckhardt, Biberach (DE); Frank Himmelsbach, Mittelbiberach (DE); Elke Langkopf, Warthausen (DE); Mohammad Tadayyon, Ulm (DE); Leo Thomas, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 412 days.

(21) Appl. No.: 11/218,057

(22) Filed: Sep. 1, 2005

(65) Prior Publication Data

US 2006/0058323 A1    Mar. 16, 2006

(30) Foreign Application Priority Data

Sep. 11, 2004    (DE) ................. 10 2004 043 944

(51) Int. Cl.
C07D 473/06    (2006.01)
C07D 519/00    (2006.01)
C07D 473/04    (2006.01)
A61K 31/522    (2006.01)
A61P 3/10    (2006.01)

(52) U.S. Cl. ............... 514/263.2; 514/263.21; 514/263.22; 514/263.35; 514/263.34; 514/263.36; 544/268; 544/269; 544/270; 544/272

(58) Field of Classification Search ................. 544/272, 544/268, 269, 270; 514/263.2, 263.21, 263.22, 514/263.34, 263.35, 263.36
See application file for complete search history.

(56) References Cited

U.S. PATENT DOCUMENTS

| | | | |
|---|---|---|---|
| 2,928,833 A | 3/1960 | Leake et al. | |
| 4,005,208 A | 1/1977 | Bender | |
| 4,599,338 A | 7/1986 | Regnier et al. | |
| 5,041,448 A | 8/1991 | Janssens | |
| 5,051,517 A | 9/1991 | Findeisen | |
| 5,223,499 A | 6/1993 | Greenlee | |
| 5,234,897 A | 8/1993 | Findeisen et al. | |
| 5,258,380 A | 11/1993 | Janssens | |
| 5,266,555 A | 11/1993 | Findeisen et al. | |
| 5,389,642 A | 2/1995 | Dorsch | |
| 5,470,579 A | 11/1995 | Bonte et al. | |
| 5,719,279 A | 2/1998 | Kuefner-Muhl et al. | |
| 5,753,635 A | 5/1998 | Buckman | |
| 6,303,661 B1 | 10/2001 | Demuth | |
| 6,342,601 B1 | 1/2002 | Bantick | |
| 6,548,481 B1 | 4/2003 | Demuth et al. | |
| 6,579,868 B1 | 6/2003 | Asano | |
| 6,784,195 B2 | 8/2004 | Hale et al. | |
| 6,821,978 B2 | 11/2004 | Chackalamannil | |
| 6,869,947 B2 | 3/2005 | Kanstrup | |
| 7,060,722 B2 | 6/2006 | Kitajima | |
| 7,074,794 B2 | 7/2006 | Kitajima | |
| 7,074,798 B2 | 7/2006 | Yoshikawa | |
| 7,074,923 B2 | 7/2006 | Dahanukar | |
| 7,109,192 B2 | 9/2006 | Hauel | |
| 7,179,809 B2 | 2/2007 | Eckhardt | |
| 7,183,280 B2 * | 2/2007 | Himmelsbach et al. | ..... 514/248 |
| 7,192,952 B2 | 3/2007 | Kanstrup | |
| 7,217,711 B2 | 5/2007 | Eckhardt | |
| 7,235,538 B2 | 6/2007 | Kanstrup et al. | |
| 2002/0161001 A1 | 10/2002 | Kanstrup | |
| 2002/0169174 A1 | 11/2002 | Chackalamannil et al. | |
| 2002/0198205 A1 * | 12/2002 | Himmelsbach et al. | .. 514/234.5 |
| 2003/0105077 A1 | 6/2003 | Kanstrup et al. | |
| 2003/0199528 A1 | 10/2003 | Kanstrup | |
| 2003/0232987 A1 | 12/2003 | Dahanukar et al. | |
| 2003/0236272 A1 | 12/2003 | Carr | |
| 2004/0034014 A1 | 2/2004 | Kanstrup et al. | |
| 2004/0077645 A1 * | 4/2004 | Himmelsbach et al. | .. 514/234.5 |
| 2004/0082570 A1 | 4/2004 | Yoshikawa | |
| 2004/0087587 A1 | 5/2004 | Himmelsbach | |
| 2004/0097510 A1 * | 5/2004 | Himmelsbach et al. | ..... 514/248 |
| 2004/0116328 A1 | 6/2004 | Yoshikawa et al. | |
| 2004/0122228 A1 | 6/2004 | Maier | |
| 2004/0138214 A1 * | 7/2004 | Himmelsbach et al. | .. 514/230.5 |

(Continued)

FOREIGN PATENT DOCUMENTS

CA    2136288 A1    5/1995

(Continued)

OTHER PUBLICATIONS

"Patient Information Januvia™" <http://www.merck.com/product/usa/pi_circulars/j/januvia/januvia_ppi.pdf> downloaded from the internet Apr. 30, 2008.*

(Continued)

*Primary Examiner*—Mark L Berch
(74) *Attorney, Agent, or Firm*—Michael P. Morris; Mary-Ellen M. Devlin; David L. Kershner

(57) ABSTRACT

The application relates to new substituted xanthines of general formula

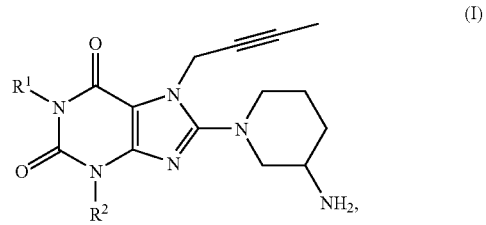

(I)

wherein $R^1$ and $R^2$ are defined as in claims 1 to 11, the tautomers, the enantiomers, the diastereomers, the mixtures thereof and the salts thereof, which have valuable pharmacological properties, particularly an inhibiting effect on the activity of the enzyme dipeptidylpeptidase-IV (DPP-IV).

13 Claims, No Drawings

U.S. PATENT DOCUMENTS

| | | | |
|---|---|---|---|
| 2004/0138215 A1* | 7/2004 | Eckhardt et al. | 514/234.5 |
| 2004/0166125 A1* | 8/2004 | Himmelsbach et al. | 424/400 |
| 2005/0020574 A1 | 1/2005 | Hauel et al. | |
| 2005/0026921 A1 | 2/2005 | Eckhardt | |
| 2005/0130985 A1 | 6/2005 | Himmelsbach | |
| 2005/0171093 A1 | 8/2005 | Eckhardt et al. | |
| 2005/0187227 A1* | 8/2005 | Himmelsbach et al. | 514/263.22 |
| 2005/0203095 A1 | 9/2005 | Eckhardt | |
| 2005/0234108 A1* | 10/2005 | Himmelsbach et al. | 514/345 |
| 2005/0261352 A1 | 11/2005 | Eckhardt | |
| 2006/0004074 A1 | 1/2006 | Eckhardt | |
| 2006/0063787 A1 | 3/2006 | Yoshikawa | |
| 2006/0079541 A1 | 4/2006 | Langkopf | |
| 2006/0094722 A1 | 5/2006 | Yasuda | |
| 2006/0142310 A1* | 6/2006 | Pfrengle et al. | 514/263.22 |
| 2006/0173056 A1 | 8/2006 | Kitajima | |
| 2006/0205711 A1 | 9/2006 | Himmelsbach | |
| 2006/0247226 A1 | 11/2006 | Himmelsbach | |
| 2007/0027168 A1* | 2/2007 | Pfrengle et al. | 514/263.22 |
| 2007/0088038 A1 | 4/2007 | Eckhardt | |
| 2007/0093659 A1 | 4/2007 | Bonfanti | |
| 2007/0142383 A1 | 6/2007 | Eckhardt | |
| 2007/0185091 A1 | 8/2007 | Himmelsbach et al. | |
| 2007/0219178 A1 | 9/2007 | Muramoto | |
| 2007/0259900 A1* | 11/2007 | Sieger et al. | 514/266.2 |
| 2007/0281940 A1* | 12/2007 | Dugi et al. | 514/248 |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2590912 A1 | 6/2006 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | 02/02560 A2 | 1/2002 |
| WO | 02/14271 A1 | 2/2002 |
| WO | 02/24698 A1 | 3/2002 |
| WO | WO 02/068420 | 9/2002 |
| WO | 03/004496 A1 | 1/2003 |
| WO | 03/024965 A2 | 3/2003 |
| WO | 03/057200 A2 | 7/2003 |
| WO | 03/104229 A1 | 12/2003 |
| WO | 2004/018467 A2 | 3/2004 |
| WO | 2004/018468 A2 | 3/2004 |
| WO | 2004/028524 A1 | 4/2004 |
| WO | 2004/033455 A2 | 4/2004 |
| WO | 2004/041820 A1 | 5/2004 |
| WO | 2004/048379 A1 | 6/2004 |
| WO | 2004/050658 A1 | 6/2004 |
| WO | WO 2004/046148 | 6/2004 |
| WO | 2004/096806 A1 | 11/2004 |
| WO | 2004/108730 A1 | 12/2004 |
| WO | 2004/111051 A1 | 12/2004 |
| WO | 2005/058901 A1 | 6/2005 |
| WO | WO 2005/082906 | 9/2005 |
| WO | WO 2005/085246 | 9/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |

OTHER PUBLICATIONS

U.S. Appl. No. 11/744,701, filed May 4, 2007, Kohlrausch.

Augustyns, K. et al., The Unique Properties of Dipeptidyl-peptidase IV (DPP IV/CD 26) and the Therapeutic Potential of DPP-IV Inhibitors, Current Medicinal Chemsitry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Deacon, C.F. et al; "Dipeptidyl peptidase IV inahibation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8, pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors, (2003).

Patani George A. et al.: "Bioisoterism : A Rational Approach in Drug Design", Chemical Reviews, 1996, vol. 96, No. 8, pp. 3147-3176.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

\* cited by examiner

8-(3-AMINO-PIPERIDIN-1-YL)-7-(BUT-2-YNYL)-XANTHINES, THE PREPARATION THEREOF AND THEIR USE AS PHARMACEUTICAL COMPOSITIONS

The present invention relates to new substituted xanthines of general formula

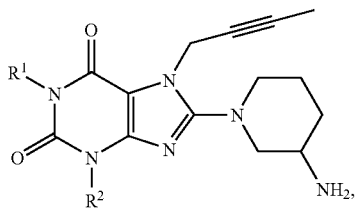

(I)

the tautomers, the enantiomers, the diastereomers, the mixtures thereof and the salts thereof, particularly the physiologically acceptable salts thereof with inorganic or organic acids which have valuable pharmacological properties, particularly an inhibiting effect on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof and processes for the preparation thereof.

Related xanthines are described in International Applications WO 02/068420, WO 04/018468, WO 04/018467, WO 04/041820 and WO 04/046148.

In the above formula I $R^1$ denotes an arylmethyl or arylethyl group, a heteroarylmethyl or heteroarylethyl group, an arylcarbonylmethyl group, a heteroarylcarbonylmethyl group or an arylprop-2-enyl or heteroarylprop-2-enyl group, wherein the propenyl chain may be substituted by 1 to 4 fluorine atoms or a cyano, $C_{1-3}$-alkyloxy-carbonyl or nitro group, and $R^2$ denotes a $C_{1-6}$-alkyl group substituted by a tetrazolyl, hydroxysulphonyl, cyano, piperidin-1-ylcarbonyl or pyrrolidin-1-ylcarbonyl group, while in the above-mentioned piperidinyl and pyrrolidinyl groups one or two methylene groups may be replaced independently of one another by an oxygen or sulphur atom, by an imino group optionally substituted by a $C_{1-4}$-alkyl group or by a carbonyl, sulphinyl or sulphonyl group, or a $C_{1-6}$-alkyl group substituted by a group of formula $R_a$—O—CO, $(R_a)_2$N—CO or $[(R_aO)_2PO$—]-wherein $R_a$ each independently denote a hydrogen atom, a $C_{1-6}$-alkyl, $C_{2-6}$-alkenyl, $C_{2-6}$-alkynyl, aryl-$C_{1-3}$-alkyl, heteroaryl-$C_{1-3}$-alkyl, $C_{3-10}$-cycloalkyl-$C_{1-3}$-alkyl, $C_{5-10}$-cycloalkenyl-$C_{1-3}$-alkyl, aryl, heteroaryl, $C_{3-10}$-cycloalkyl or $C_{5-10}$-cycloalkenyl group, while all the alkyl, alkenyl, alkynyl, cycloalkyl and cycloalkenyl groups mentioned for $R_a$ may be partly or completely fluorinated or mono- to disubstituted by identical or different substituents selected from chlorine, hydroxy, $C_{1-3}$-alkoxy and $C_{1-3}$-alkyl, and in the cycloalkyl and cycloalkenyl groups mentioned for $R_a$ one or two methylene groups may be replaced independently of one another by an oxygen or sulphur atom, by an imino group optionally substituted by a $C_{1-4}$-alkyl group or by a carbonyl, sulphinyl or sulphonyl group, while by the aryl groups mentioned in the definition of the above groups are meant phenyl or naphthyl groups, which may be mono-, di- or trisubstituted by $R_h$ independently of one another, while the substituents may be identical or different and $R_h$ denotes a fluorine, chlorine, bromine or iodine atom, a trifluoromethyl, cyano, nitro, amino, aminocarbonyl, $C_{1-3}$-alkoxy-carbonyl, aminosulphonyl, methylsulphonyl, acetylamino, methylsulphonylamino, $C_{1-3}$-alkyl, cyclopropyl, ethenyl, ethynyl, phenyl, morpholinyl, hydroxy, $C_{1-3}$-alkyloxy, difluoromethoxy or trifluoromethoxy group, or two $R_h$ at two adjacent carbon atoms of the aromatic group together form a $C_{3-5}$-alkylene chain, while in the alkylene chain one or two methylene groups may be substituted independently of one another by oxygen atoms or carbonyl groups, and additionally each hydrogen atom may be replaced by a fluorine atom, by the heteroaryl groups mentioned in the definition of the above-mentioned groups are meant a pyrrolyl, furanyl, thienyl, pyridyl, indolyl, benzofuranyl, benzothiophenyl, phenanthridinyl, quinolinyl or isoquinolinyl group, or a pyrrolyl, furanyl, thienyl, imidazolyl or pyridyl group, wherein one or two methyne groups are replaced by nitrogen atoms, or an indolyl, benzofuranyl, benzothiophenyl, phenanthridinyl, quinolinyl or isoquinolinyl group, wherein one to three methyne groups are replaced by nitrogen atoms, or a 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1oxo-isoquinolinyl, 1,4-dihydro-4-oxo-cinnolinyl, 1,2-dihydro-2-oxo-quinazolinyl, 3,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, cumarinyl, 2,3-dihydro-benzo[1,4]dioxinyl, imidazo[1,2-a]quinolinyl, benzo[1,6]naphthyridinyl, 3H-quinzaolin-4-onyl, 1H-quinolin-2-onyl or 3,4-dihydro-3-oxo-2H-benzo[1,4]oxazinyl group, and the above-mentioned heteroaryl groups may be mono- or disubstituted by $R_h$, while the substituents may be identical or different and $R_h$ is as hereinbefore defined, by the cycloalkyl and cycloalkenyl groups mentioned in the above definitions are meant both monocyclic and polycyclic ring systems, while the polycyclic groups may be of annelated, spiro-linked or bridged structure, for example the term polycyclic groups denotes decalin, octahydroindene, norbornane, spiro[4.4]nonane, spiro[4.5]decane, bicyclo[2.1.1]hexane, bicyclo[2.2.2]octane, bicyclo[3.2.1]octane, bicyclo[3.2.2]nonane, bicyclo[3.3.1]nonane, bicyclo[3.3.2]decane or adamantane or the monounsaturated derivatives thereof, while, unless otherwise stated, the above-mentioned alkyl, alkenyl and alkynyl groups may be straight-chain or branched, the tautomers, enantiomers, diastereomers, the mixtures thereof, the prodrugs thereof and the salts thereof.

The carboxy groups mentioned in the definition of the abovementioned groups may be replaced by a group which can be converted into a carboxy group in vivo or by a group which is negatively charged under physiological conditions, and furthermore the amino and imino groups mentioned in the definition of the abovementioned groups may be substituted by a group which can be cleaved in vivo. Such groups are described for example in WO 98/46576 and by N. M. Nielsen et al. in International Journal of Pharmaceutics 39, 75-85 (1987).

By a group which can be converted in vivo into a carboxy group is meant, for example, a hydroxymethyl group, a carboxy group esterified with an alcohol wherein the alcohol moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bonds to the oxygen atom start from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

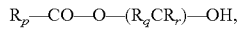

$R_p$—CO—O—$(R_qCR_r)$—OH, wherein $R_p$ denotes a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group, $R_q$ denotes a hydrogen atom, a $C_{1-3}$-alkyl, $C_{5-7}$-cycloalkyl or phenyl group and $R_r$ denotes a hydrogen atom or a $C_{1-3}$-alkyl group, by a group which is negatively charged under physiological conditions is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as a phenylcarbonyl group optionally mono- or disubstituted by fluorine, chlorine, bromine or iodine atoms, by $C_{1-3}$-alkyl or $C_{1-3}$-alkoxy groups, while the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkoxycarbonyl or $C_{1-16}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkoxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_p$—CO—O—$(R_qCR_r)$—O—CO—, $C_{1-6}$-alkyl-CO—NH—$(R_sCR_t)$—O—CO— or $C_{1-6}$-alkyl-CO—O—$(R_sCR_t)$—$(R_sCR_t)$—O—CO— group, wherein $R_p$ to $R_r$ are as hereinbefore defined, $R_s$ and $R_t$, which may be identical or different, denote hydrogen atoms or $C_{1-3}$-alkyl groups.

Moreover, unless otherwise stated, the saturated alkyl and alkoxy moieties containing more than 2 carbon atoms mentioned in the definitions above also include the branched isomers thereof such as the isopropyl, tert.butyl, isobutyl group, etc.

$R^1$ may denote for example a 2-cyanobenzyl, 3-cyanobenzyl, 2-fluorobenzyl, 3-fluorobenzyl, 3-methoxybenzyl, 4-bromo-2-cyanobenzyl, 3-chloro-2-cyanobenzyl, 2-cyano-4-fluorobenzyl, 2-cyano-5-fluorobenzyl, 2-cyano-6-fluorobenzyl, 4-cyano-3-fluorobenzyl, 4-cyano-3-nitrobenzyl, 3,5-dimethoxybenzyl, 2-cyano-3-methoxybenzyl, 2-cyano-4-methoxybenzyl, 2-cyano-5-methoxybenzyl, 2,6-dicyanobenzyl, 3,4-dicyanobenzyl, 3,5-dicyanobenzyl, 5-cyanofuranylmethyl, oxazolylmethyl, isoxazolylmethyl, 5-methoxycarbonylthienylmethyl, pyridinylmethyl, 3-cyanopyridin-2-ylmethyl, 6-cyanopyridin-2-ylmethyl, 6-fluoropyridin-2-ylmethyl, pyrimidin-2-yl, 4-methylpyrimidin-2-yl, 4,6-dimethylpyrimidin-2-yl, 3-(2-cyanophenyl)-prop-2-enyl, 3-(2-nitrophenyl)-prop-2-enyl, 3-(pyridin-2-yl)-prop-2-enyl, 3-(pentafluorophenyl)-prop-2-enyl, phenylcarbonylmethyl, 3-methoxyphenylcarbonylmethyl, 1-methyl-benzotriazol-5-ylmethyl, naphth-1-ylmethyl, 4-cyanonaphth-1-ylmethyl, 4-fluoronaphth-1-ylmethyl, 4-bromonaphth-1-ylmethyl, 4-methoxynaphth-1-ylmethyl, quinolin-1-ylmethyl, 4-cyanoquinolin-1-ylmethyl, 8-cyanoquinolin-7-ylmethyl, isoquinolin-1-ylmethyl, 4-cyanoisoquinolin-1-ylmethyl, 3-methylisoquinolin-1-ylmethyl, quinazolin-2-ylmethyl, 4-methylquinazolin-2-ylmethyl, 4-cyanoquinazolin-2-ylmethyl, 4-aminoquinazolin-2-ylmethyl, 4-morpholin-4-ylquinazolin-2-ylmethyl, [1,5]naphthiridin-2-ylmethyl, [1,5]naphthiridin-3-ylmethyl, phenanthridin-6-ylmethyl, quinoxalin-6-ylmethyl or 2,3-dimethyl-quinoxalin-6-ylmethyl group.

$R^2$ may denote for example a cyanomethyl, cyanoethyl, cyanopropyl, carboxymethyl, carboxyethyl, carboxypropyl, methoxycarbonylmethyl, methoxycarbonylethyl, methoxycarbonylpropyl, ethoxycarbonylmethyl, ethoxycarbonylethyl, ethoxycarbonylpropyl, isopropoxycarbonylmethyl, isopropoxycarbonylethyl, isopropoxycarbonylpropyl, propoxycarbonylmethyl, propoxycarbonylethyl, propoxycarbonylpropyl, allyloxycarbonylmethyl, propargyloxycarbonylmethyl, butoxycarbonylmethyl, tert-butoxycarbonylmethyl, benzyloxycarbonylmethyl or p-methoxybenzylcarbonylmelthyl group.

Preferred compounds of general formula I are those wherein $R^1$ is as hereinbefore defined, and $R^2$ denotes a $C_{1-4}$-alkyl group substituted by a cyano group or a group of formula $R_a$—O—CO—, where $R_a$ is as hereinbefore defined, the enantiomers, the diastereomers, the mixtures thereof and the salts thereof.

Particularly preferred are those compounds of general formula I wherein $R^1$ denotes a phenylmethyl, phenylcarbonylmethyl, phenylprop-2-enyl, pyridinylmethyl, pyrimidinylmethyl, naphthylmethyl, quinolinylmethyl, 1H-quinolin-2-onylmethyl, imidazo[1,2-a]quinolinylmethyl, isoquinolinylmethyl, quinazolinylmethyl, 3H-quinazolin-4-onylmethyl, quinoxalinylmethyl, phenanthridinylmethyl, naphthyridinylmethyl, benzo[1,6]naphthiridinylmethyl, imidazopyridinylmethyl or benzotriazolylmethyl group which may be substituted in each case by one or two fluorine, chlorine or bromine atoms or by one or two cyano, nitro, amino, $C_{1-3}$-alkyl, $C_{1-3}$-alkyloxy, phenyl or morpholinyl groups, while the substituents may be identical or different, and $R^2$ denotes a cyano-$C_{1-3}$-alkyl, hydroxycarbonylmethyl, $C_{1-6}$-alkyloxycarbonylmethyl, $C_{3-6}$-alkenyloxycarbonylmethyl, $C_{3-6}$-cycloalkyl-$C_{1-3}$-alkyloxycarbonylmethyl or $C_{3-6}$-cycloalkyloxycarbonylmethyl group, while the alkyl, alkenyl and cycloalkyl groups may each be substituted by one or two $C_{1-3}$-alkyl or $C_{1-3}$-alkyloxy groups and/or partly or completely fluorinated, the enantiomers, the diastereomers, the tautomers, the mixtures thereof and the salts thereof.

Most particularly preferred are those compounds of general formula I wherein $R^1$ denotes a pyridinylmethyl, pyrimidinylmethyl, isoquinolinylmethyl, quinazolinylmethyl, quinoxalinylmethyl or naphthylmethyl group which may be substituted by one or two cyano or methyl groups, and $R^2$ denotes a cyanomethyl, hydroxycarbonylmethyl, methoxycarbonylmethyl or ethoxycarbonylmethyl group, the enantiomers, the tautomers and the salts thereof.

A preferred sub-group comprises those compounds of general formula I wherein $R^1$ denotes a quinazolinylmethyl group which may be substituted by a methyl group, and $R^2$ denotes a methyl group substituted by a $C_{1-4}$-alkoxycarbonyl group, the enantiomers, the tautomers and the salts thereof.

The following preferred compounds are mentioned by way of example:
(a) 1-(naphthyl-1-ylmethyl)-3-(methoxycarbonylmethyl)-7-(but-2-ynyl)-8-(3-amino-piperidin-1-yl)-xanthine
(b) 1-(naphthyl-1-ylmethyl)-3-(cyanomethyl)-7-(but-2-ynyl)-8-(3-amino-piperidin-1-yl)-xanthine
(c) (R)-1-(4-methyl-quinazolin-2-ylmethyl)-3-(methoxycarbonylmethyl)-7-(but-2-ynyl)-8-(3-amino-piperidin-1-yl)-xanthine
(d) (R)-1-(4-methyl-quinazolin-2-ylmethyl)-3-(ethoxycarbonylmethyl)-7-(but-2-ynyl)-8-(3-amino-piperidin-1-yl)-xanthine
(e) (R)-1-(4-methyl-quinazolin-2-ylmethyl)-3-(hydroxycarbonylmethyl)-7-(but-2-ynyl)-8-(3-amino-piperidin-1-yl)-xanthine and the tautomers and the salts thereof.

According to the invention the compounds of general formula I are obtained by methods known per se, for example by the following methods:

a) reacting a compound of general formula

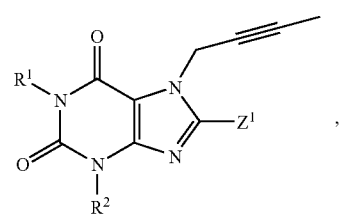

(II)

wherein $R^1$ and $R^2$ are as hereinbefore defined and $Z^1$ denotes a leaving group such as a halogen atom, a substituted hydroxy, mercapto, sulphinyl, sulphonyl or sulphonyloxy group such as e.g. a chlorine, bromine or iodine atom, a methanesulphonyl, trifluoromethanesulphonyloxy or methanesulphonyloxy group, with 3-aminopiperidine, a 3-N-protected aminopiperidine, a derivative or salts thereof.

Protecting groups for the 3-amino group might be, for example, the formyl, acetyl, trifluoroacetyl, ethoxycarbonyl, tert.-butoxycarbonyl, allyloxycarbonyl, benzyloxy-carbonyl, p-methoxybenzylcarbonyl, benzyl, methoxybenzyl, 2,4-dimethoxybenzyl, phthalyl or tetrachlorophthalyl group. However, the amino group may also be part of a heteroaromatic group, for example, such as e.g. 2,5-dimethylpyrrole and may be released therefrom at a later stage.

The 3-amino function may also be masked in the form of a carboxy group or a derivative thereof, which may be converted into the amino function by so-called Curtius, Schmidt or Hofmann degradation (cf inter alia J. March, Advanced Organic Reactions, Reactions, Mechanisms, and Structure, 4th Edition, John Wiley & Sons, Chichester/New York/Brisbane/Toronto/Singapore, 1992 and literature cited therein).

The reaction is expediently carried out in a solvent such as isopropanol, butanol, tetrahydrofuran, dioxane, dimethylformamide, dimethylsulphoxide, ethyleneglycol monomethyl ether, ethyleneglycol diethyl ether or sulpholane, optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously also serve as solvent, and optionally in the presence of a reaction accelerator such as an alkali metal halide or a palladium- or copper-based catalyst at temperatures between −20 and 180° C., but preferably at temperatures between −10 and 120° C. The reaction may, however, also be carried out without a solvent in an excess of piperidine derivative with conventional heating or in the microwave oven.

b) deprotecting a compound of general formula

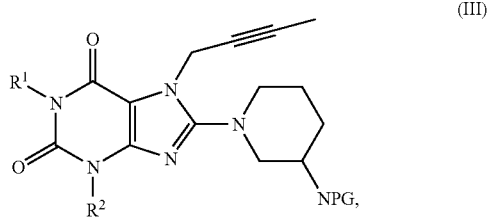

(III)

wherein R¹ and R² are as hereinbefore defined and

NPG denotes a protected or masked amino functionality. Possible protective groups or maskings of the amino function have already been mentioned under a). Preferably the amino group is protected by a tert.-butoxycarbonyl or phthalyl group.

The tert.-butyloxycarbonyl group is preferably cleaved by treating with an acid such as trifluoroacetic acid or hydrochloric acid or by treating with bromotrimethylsilane or iodotrimethylsilane, optionally using a solvent such as methylene chloride, ethyl acetate, dioxane, methanol, isopropanol or diethyl ether, at temperatures between 0 and 80° C. The phthalyl group is preferably cleaved in the presence of hydrazine or a primary amine such as methylamine, ethylamine, ethanolamine or n-butylamine in a solvent such as methanol, ethanol, isopropanol, toluene, toluene/water or dioxane, at temperatures between 20 and 120° C.

In the reactions described hereinbefore, any reactive groups present such as amino, alkylamino or imino groups may be protected during the reaction by conventional protecting groups which are cleaved again after the reaction.

For example, protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably from 3 to 5 bar. However, a 2,4-dimethoxybenzyl group is preferably cleaved in trifluoroacetic acid in the presence of anisole.

A tert.-butyl or tert. butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid, at temperatures between 50 and 120° C. or by treating with sodium hydroxide solution, optionally in the presence of a solvent such as tetrahydrofuran, at temperatures between 0 and 50° C.

A phthalyl group is preferably cleaved in the presence of hydrazine or a primary amine such as methylamine, ethylamine or n-butylamine in a solvent such as methanol, ethanol, ethanolamine, isopropanol, toluene, toluene/water or dioxane at temperatures between 20 and 120° C.

The liberation of an amino function from 2,5-dimethylpyrrole is carried out, for example, with hydroxylamine hydrochloride in the presence of a base such as e.g. triethylamine, in a suitable solvent such as an alcohol, such as e.g. methanol, ethanol, propanol or isopropanol or water or mixtures thereof, at temperatures between 0 and 150° C., but preferably at ambient temperatures between 50 and 110° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be separated by chromatography into their cis and trans isomers, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-p-toluoyltartaric acid, malic acid, mandelic acid, camphorsulphonic acid, glutamic acid, aspartic acid or quinic acid. An optically active alcohol may be, for example, (+)- or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the new compounds of formula I, if they contain a carboxy group, may if desired be converted into the salts thereof with inorganic or organic bases, particularly for pharmaceutical use into the physiologically acceptable salts thereof. Suitable bases for this include, for example, sodium hydroxide, potassium hydroxide, cyclohexylamine, ethanolamine, diethanolamine and triethanolamine.

The compounds of general formulae Ii and III used as starting compounds are either known from the literature or may be prepared by methods known from the literature (see Examples I to VI).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2", which appeared in Proc. Natl. Acad. Sci. Vol. 90, pp. 5757-5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 µl of substrate solution (AFC; AFC is amido-4-trifluoromethylcoumarin), final concentration 100 µM, were placed in black microtitre plates. 20 µl of assay buffer (final concentrations 50 mM Tris HCl pH 7.8, 50 mM NaCl, 1% DMSO) was pipetted in. The reaction was started by the addition of 30 µl of solubilised Caco-2 protein (final concentration 0.14 µg of protein per well). The test substances under investigation were typically added prediluted to 20 µl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potency of the test substances in question, expressed as $IC_{50}$ values, were calculated from dosage/activity curves consisting of 11 measured points in each case. The following results were obtained:

| Compound (Example No.) | DPP IV inhibition $IC_{50}$ [nM] |
|---|---|
| 1(2) | 3 |
| 1(3) | 3 |

The compounds prepared according to the invention are well tolerated as no toxic side effects could be detected in rats after the oral administration of 10 mg/kg of the compound of Example 1(2), for example.

In view of their ability to inhibit DPP-IV activity, the compounds of general formula I according to the invention and the corresponding pharmaceutically acceptable salts thereof are suitable for influencing any conditions or diseases which can be affected by the inhibition of the DPP-IV activity. It is therefore to be expected that the compounds according to the invention will be suitable for the prevention or treatment of diseases or conditions such as type I and type II diabetes mellitus, prediabetes, reduced glucose tolerance or changes in the fasting blood sugar, diabetic complications (e.g. retinopathy, nephropathy or neuropathies), metabolic acidosis or ketosis, reactive hypoglycaemia, insulin resistance, metabolic syndrome, dyslipidaemias of various origins, arthritis, atherosclerosis and related diseases, obesity, allograft transplantation and osteoporosis caused by calcitonin. In addition, these substances are suitable for preventing B-cell degeneration such as e.g. apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides such as e.g. GLP-1 and GLP-2 and their link with DPP-IV inhibition, it is expected that the compounds according to the invention will be suitable for achieving, inter alia, a sedative or tranquillising effect, as well as having a favourable effect on catabolic states after operations or hormonal stress responses or possibly reducing mortality and morbidity after myocardial infarction. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases such as e.g. irritable bowel syndrome (IBS), Crohn's disease or ulcerative colitis and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neuro-degenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based thyroid carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psychosomatic, depressive and neuropsychiatric diseases of all kinds.

The compounds according to the invention may also be used in conjunction with other active substances. Suitable therapeutic agents for such combinations include for example antidiabetic agents such as mefformin, sulphonylureas (e.g. glibenclamide, tolbutamide, glimepiride), nateglinide, repaglinide, thiazolidinediones (e.g. rosiglitazone, pioglitazone), PPAR-gamma agonists (e.g. GI 262570) and antagonists, PPAR-gamma/alpha modulators (e.g. KRP 297), PPAR-gamma/alpha/delta modulators, AMPK activators, ACC1 and ACC2 inhibitors, DGAT-inhibitors, SMT3 receptor agonists, 11β-HSD inhibitors, FGF19 agonists or mimetics, alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, combinations with SGLT2 inhibitors such as T-1095 or KGT-1251 (869682), inhibitors of protein tyrosine phosphatase 1, substances which influence deregulated glucose production in the liver, such as e.g. inhibitors of glucose- 6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, PPAR-alpha agonists, PPAR-delta agonists, ACAT inhibitors (e.g. avasimibe) or cholesterol absorption inhibitors such as for example ezetimibe, bile acid-binding substances such as for example cholestyramine, inhibitors of ileac bile acid transport, HDL-raising compounds such as for example inhibitors of CETP or regulators of ABC1 or LXRalpha antagonists, LXRbeta agonists or LXRalpha/beta regulators or active substances for the treatment of obesity, such as e.g. sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or $\beta_3$-agonists such as SB-418790 or AD-9677 as well as agonists of the 5HT2c receptor.

It is also possible to combine the compounds with drugs for treating high blood pressure such as e.g. AII antagonists or ACE inhibitors, diuretics, β-blockers, Ca-antagonists, etc., or combinations thereof.

The dosage required to expediently achieve such an effect is, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the starting compounds:

EXAMPLE I 1-ethoxycarbonylmethyl-3-cyano-2-phenyl-isourea 29.3 g glycinethylester hydrochloride are added to a solution of 50.0 g diphenyl-N-cyano-carbonimidate in 29 ml triethylamine and 500 ml isopropanol. The solution is stirred for 16 h (hours) at ambient temperature and then evaporated down. The residue is dissolved in ethyl acetate and the organic phase is washed with water and aqueous potassium carbonate solution. The organic phase is dried over sodium sulphate and the solvent is eliminated completely. The residue is washed with diethyl ether and dried.

Yield: 35.5 g (68% of theory) Mass spectrum (ESI$^+$): m/z=248 [M+H]$^+$

EXAMPLE II 1-ethoxycarbonylmethyl-1-(but-2-ynyl)-3-cyano-2-phenyl-isourea 11 ml of but-2-ynylbromide are added to a mixture of 30.2 g 1-ethoxycarbonylmethyl-3-cyano-2-phenyl-isourea and 20.0 g potassium carbonate in 200 ml acetone. After 1 d (day) stirring at ambient temperature a further 6.5 g potassium carbonate and 3.5 ml of but-2-ynylbromide are added. After another 20 h at ambient temperature the solvent is removed and ethyl acetate is added. The organic phase is washed with water, dried over sodium sulphate and evaporated to dryness.

Yield: 35.2 g (96% of theory) Mass spectrum (ESI$^+$): m/z=300 [M+H]$^+$

EXAMPLE III 3-tert-butoxycarbonylamino-N-(ethoxycarbonylmethyl)-N-(but-2-ynyl)-N'-cyano-piperidine-1-carboxamidine 10.0 g of 1-ethoxycarbonylmethyl-1-(but-2-ynyl)-3-cyano-2-phenyl-isourea are added to a mixture of 10.0 g 3-tert-butoxycarbonylaminopiperidine and 4.8 g potassium carbonate in 50 ml of dimethylformamide. The reaction mixture is stirred for 1 day at ambient temperature and then a further 1.6 g potassium carbonate and 3.0 g 3-tert-butoxycarbonylaminopiperidine are added. After another 3 days at ambient temperature water is added and the mixture is extracted with ethyl acetate. The organic extracts are dried over sodium sulphate, the solvent is removed and the residue is purified on silica gel (cyclohexane/ethyl acetate 5:1->1:2).

Yield: 12.5 g (approx. 90%, 83% of theory) Mass spectrum (ESI$^+$): m/z=406 [M+H]$^+$ The following compound is obtained analogously to Example III:

(1) (R)-3-tert-butoxycarbonylamino-N-(ethoxycarbonylmethyl)-N-(but-2-ynyl)-N'-cyano-piperidine-1-carboxamidine Mass spectrum (ESI$^+$): m/z=406 [M+H]$^+$

EXAMPLE IV

Ethyl 5-amino-2-(3-tert-butoxycarbonylamino-piperidin-1-yl)-3-(but-2-ynyl)-3H-imidazole-4-carboxylate 2.5 g sodium ethoxide are added to a solution of 12.5 g (approx. 90%) 3-tert-butoxycarbonylamino-N-(ethoxycarbonylmethyl)-N-(but-2-ynyl)-N'-cyano-piperidine-1-carboxamidine in 100 ml dry ethanol. The reaction solution is stirred for 3 h at ambient temperature and then neutralised with 1 M hydrochloric acid. The solvent is removed, water is added and the mixture is extracted with ethyl acetate. The organic extracts are dried over sodium sulphate, the solvent is removed and the residue is purified on silica (cyclohexane/ethyl acetate 3:1->1:5).

Yield: 5.7 g (51% of theory) Mass spectrum (ESI$^+$): m/z=406 [M+H]$^+$

The following compound is obtained analogously to Example III:

(1) ethyl 5-amino-2-(3-tert-butoxycarbonylamino-piperidin-1-yl)-3-(but-2-ynyl)-3H-imidazole-4-carboxylate Mass spectrum (ESI$^+$): m/z=406 [M+H]$^+$

EXAMPLE V 1-(naphth-1-ylmethyl)-7-(but-2-ynyl)-8-(3-tert-butoxycarbonylamino-piperidin-1-yl)-xanthine 0.5 g triphosgene and 1.4 ml triethylamine are added successively to an ice-cooled solution of 2.0 g of ethyl 5-amino-2-(3-tert-butoxycarbonylamino-piperidin-1-yl)-3-(but-2-ynyl)-3H-imidazole-4-carboxylate in 35 ml dry 1,2-dimethoxyethane. After 2 h stirring at ambient temperature 0.76 ml naphth-1-ylmethylamine and a further 35 ml dry 1,2-dimethoxyethane are added. The reaction solution is stirred for a further 14 h at ambient temperature. Then the solution is evaporated down to approx. 20 ml and diluted with 150 ml dichloromethane. The organic phase is washed with 1 M hydrochloric acid and with aqueous sodium hydrogen carbonate solution and then dried over sodium sulphate. After the solvent has been eliminated the residue is dissolved in 100 ml of ethanol and combined with 0.41 g sodium ethoxide. The solution is stirred for 4 h at 60° C. After cooling to ambient temperature the reaction solution is neutralised with 1 M hydrochloric acid and the ethanol is evaporated off. Water is added and the precipitate is separated off, washed with ether and dried at 60° C.

Yield: 2.1 g (77% of theory) Mass spectrum (ESI$^+$): m/z=543 [M+H]$^+$

The following compound is obtained analogously to Example V:

(1)(R)-1-(4-methyl-quinazolin-2-ylmethyl)-7-(but-2-ynyl)-8-(3-tert-butoxycarbonylamino-piperidin-1-yl)-xanthine Mass spectrum (ESI$^+$): m/z=559 [M+H]$^+$

Example VI 1-(naphth-1-ylmethyl)-3-(cyanomethyl)-7-(but-2-ynyl)-8-(3-tert-butoxycarbonylamino-piperidin-1-yl)-xanthine 30 µl of bromoacetonitrile are added to a mixture of 0.20 g 1-(naphth-1-ylmethyl)-7-(but-2-ynyl)-8-(3-tert-butoxycarbonylamino-piperidin-1-yl)-xanthine and 0.10 g potassium carbonate in 3 ml of dimethylformamide. The reaction mixture is stirred for 3 h at 60° C. and then cooled to ambient temperature. Water is added and the precipitate is separated off and dried at 60° C.

Yield: 0.20 g (93% of theory) Mass spectrum (ESI$^+$): m/z=582 [M+H]$^+$

The following compounds are obtained analogously to Example VI:

(1) 1-(naphth-1-ylmethyl)-3-(methoxycarbonylmethyl)-7-(but-2-ynyl)-8-(3-tert-butoxycarbonylamino-piperidin-1-yl)-xanthine Mass spectrum (ESI$^+$): m/z=615 [M+H]$^+$ (2) (R)-1-(4-methyl-quinazolin-2-ylmethyl)-3-(methoxycarbonylmethyl)-7-(but-2-ynyl)-8-(3-tert-butoxycarbonylamino-piperidin-1-yl)-xanthine Mass spectrum (ESI$^+$): m/z=631 [M+H]$^+$ (3) (R)-1-(4-methyl-quinazolin-2-ylmethyl)-3-(ethoxycarbonylmethyl)-7-(but-2-ynyl)-8-(3-tert-butoxycarbonylamino-piperidin-1-yl)-xanthine Mass spectrum (ESI$^+$): m/z=645 [M+H]$^+$ Preparation of the end compounds:

EXAMPLE 1

1-(naphth-1-ylmethyl)-3-(methoxycarbonylmethyl)-7-(but-2-ynyl)-8-(3-amino-piperidin-1-yl)-xanthine

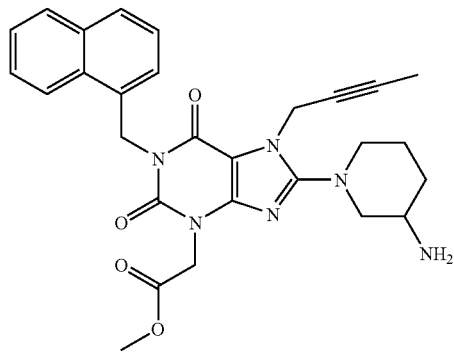

0.7 ml of trifluoroacetic acid are added to a solution of 200 mg 1-(naphth-1-ylmethyl)-3-(methoxycarbonylmethyl)-7-(but-2-ynyl)-8-(3-tert-butoxycarbonylamino-piperidin-1-yl)-xanthine in 3 ml dichloromethane. The solution is stirred for 3 h at ambient temperature and then added to ice-cooled aqueous potassium carbonate solution. The aqueous phase is extracted with dichloromethane, the combined organic extracts are dried over sodium sulphate, and the solvent is removed. The residue is purified by chromatography on a silica gel column with methylene chloride/methanol (7:3) as eluant.

Yield: 85 mg (29% of theory) Mass spectrum (ESI$^+$): m/z=515 [M+H]$^+$

The following compounds are obtained analogously to Example 1:

(1) 1-(naphth-1-ylmethyl)-3-(cyanomethyl)-7-(but-2-ynyl)-8-(3-amino-piperidin-1-yl)-xanthine

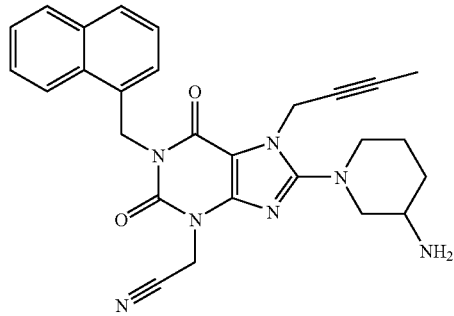

Mass spectrum (ESI$^+$): m/z=482 [M+H]$^+$ (2) (R)-1-(4-methyl-quinazolin-2-ylmethyl)-3-(methoxycarbonylmethyl)-7-(but-2-ynyl)-8-(3-amino-piperidin-1-yl)-xanthine

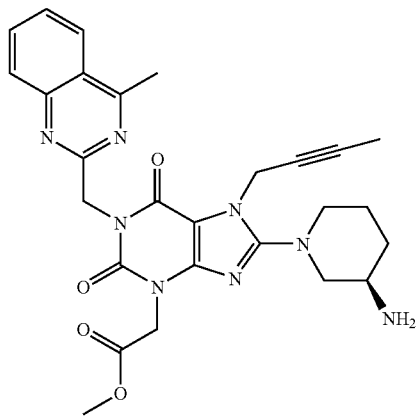

Mass spectrum (ESI⁺): m/z=531 [M+H]⁺

(3) (R)-1-(4-methyl-quinazolin-2-ylmethyl)-3-(ethoxycarbonylmethyl)-7-(but-2-ynyl)-8-(3-amino-piperidin-1-yl)-xanthine

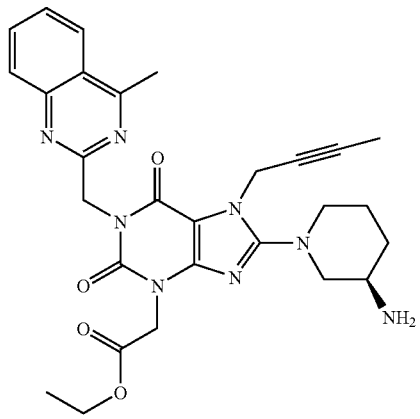

Mass spectrum (ESI⁺): m/z=545 [M+H]⁺

EXAMPLE 2

(R)-1-(4-methyl-quinazolin-2-ylmethyl)-3-(hydroxycarbonylmethyl)-7-(but-2-ynyl)-8-(3-amino-piperidin-1-yl)-xanthine

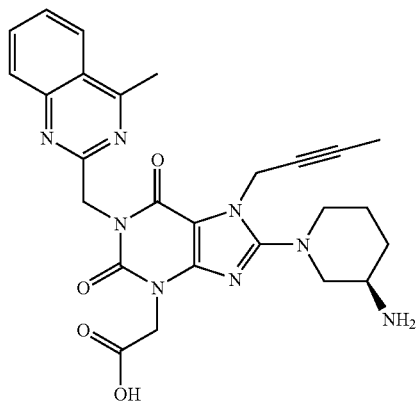

2 ml of 1 M sodium hydroxide solution are added to a solution of 150 mg of (R)-1-(4-methyl-quinazolin-2-ylmethyl)-3-(methoxycarbonylmethyl)-7-(but-2-ynyl)-8-(3-amino-piperidin-1-yl)-xanthine in 6 ml of tetrahydrofuran/water/methanol (1:1:1). The solution is stirred for 1 h at ambient temperature and then neutralised with 1 M hydrochloric acid. The solution is evaporated to dryness and purified by HPLC (YMC-C18) with water/acetonitrile (70:30).

Yield: 120 mg (82% of theory) Mass spectrum (ESI⁺): m/z=517 [M+H]⁺

The following compounds may also be obtained analogously to the foregoing Examples and other methods known from the literature:

| Ex. | Structure |
|---|---|
| (1) | 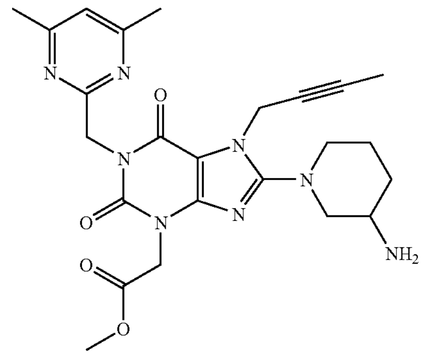 |
| (2) | 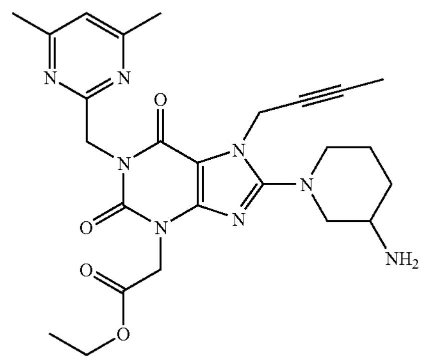 |
| (3) | 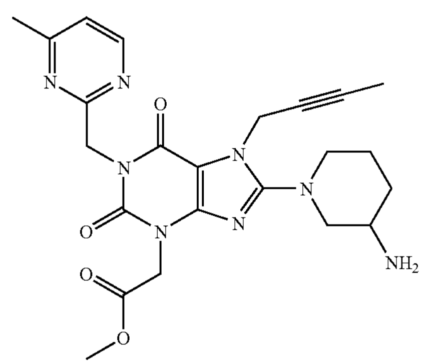 |

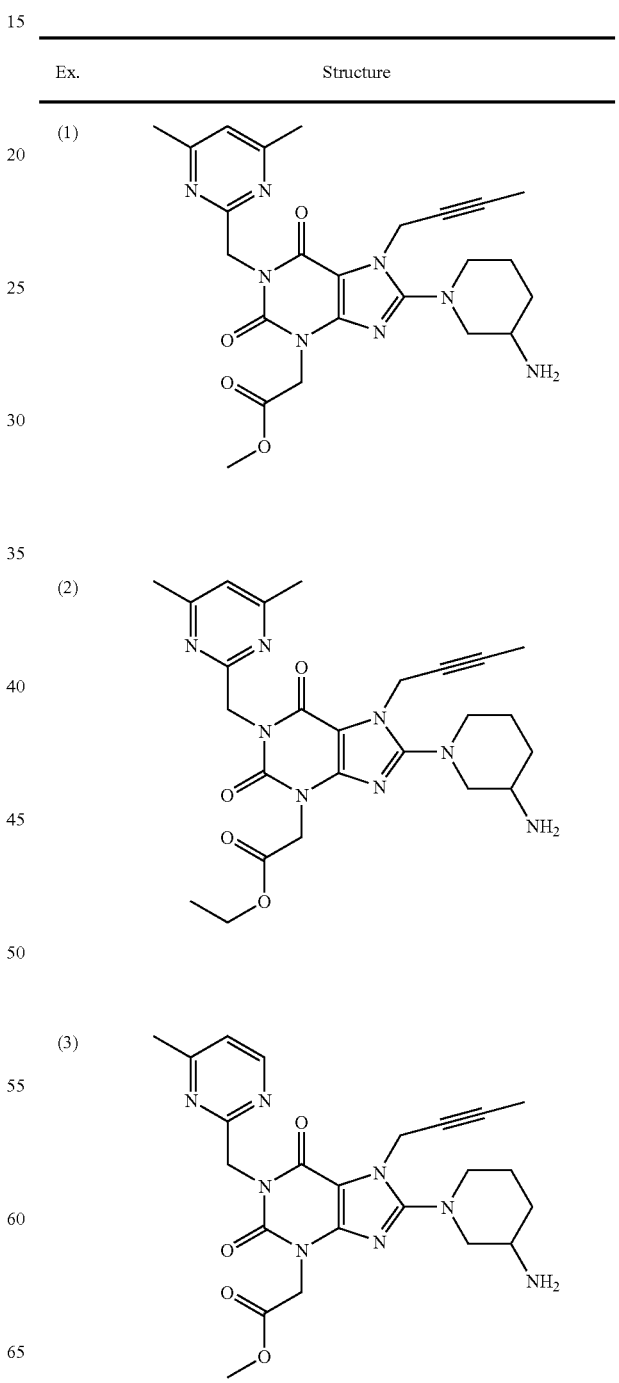

| Ex. | Structure |
|---|---|
| (4) | 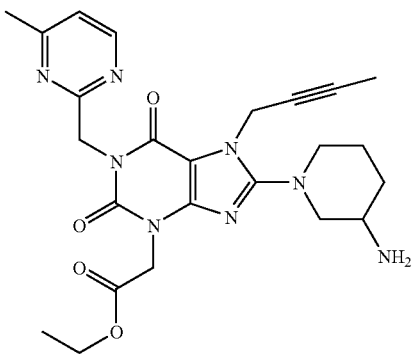 |
| (5) | 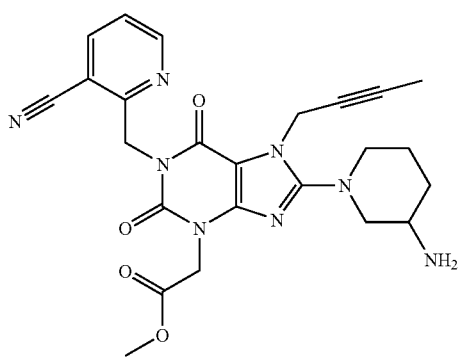 |
| (6) | 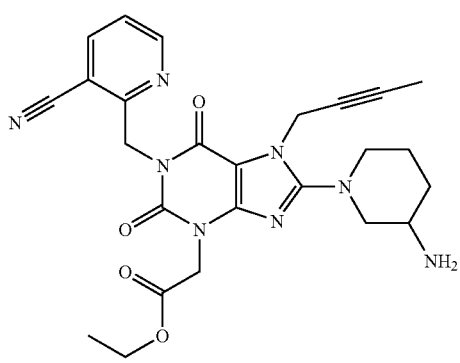 |
| (7) | 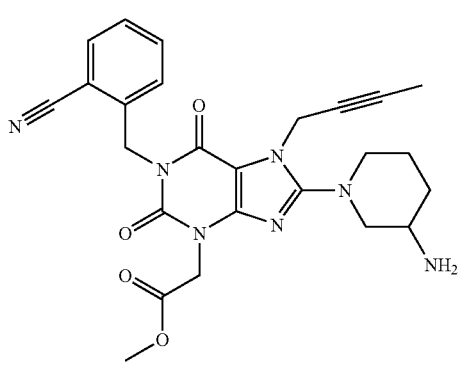 |
| (8) | 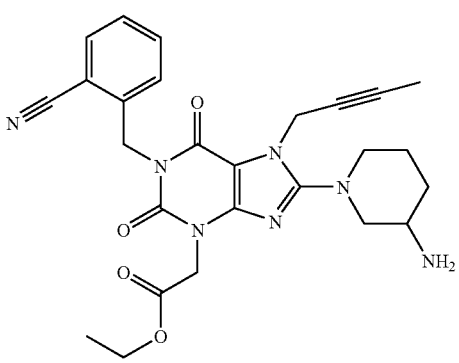 |
| (9) | 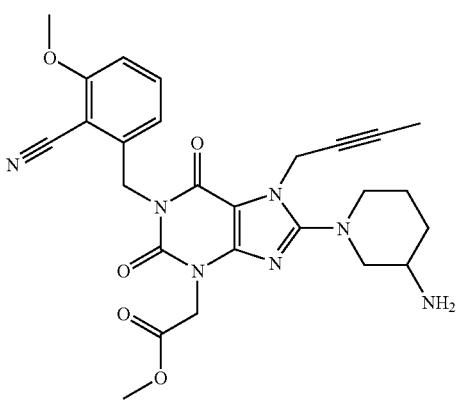 |
| (10) | 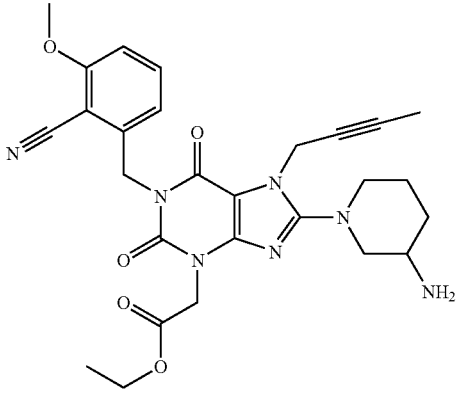 |
| (11) | 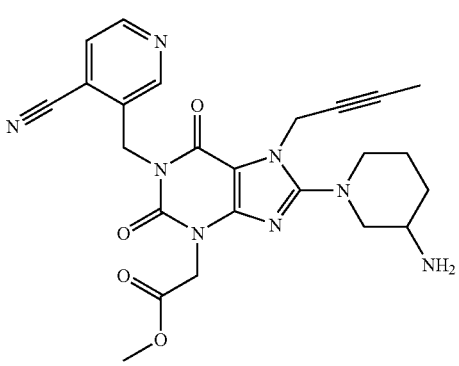 |

| Ex. | Structure |
|---|---|
| (12) | 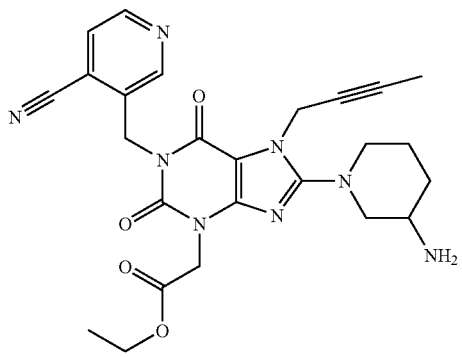 |
| (13) | 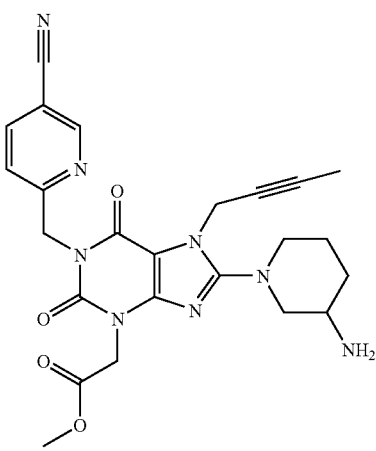 |
| (14) | 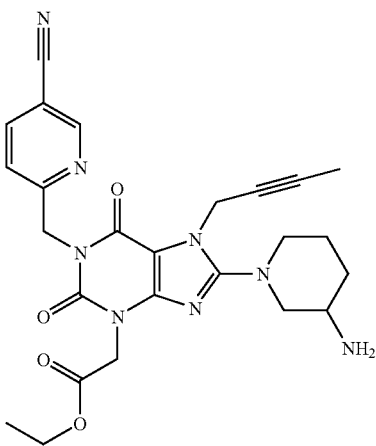 |
| Ex. | Structure |
|---|---|
| (15) | 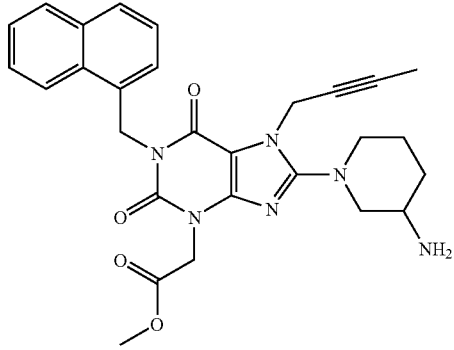 |
| (16) | 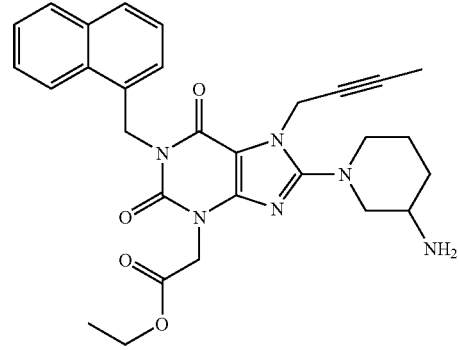 |
| (17) | 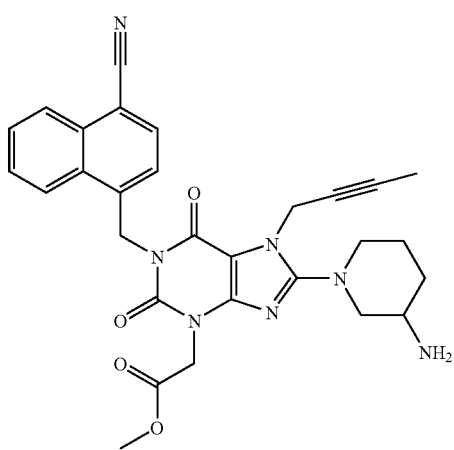 |

| Ex. | Structure |
|---|---|
| (18) | 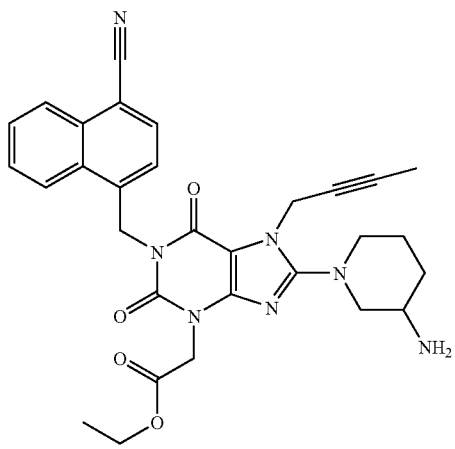 |
| (19) | 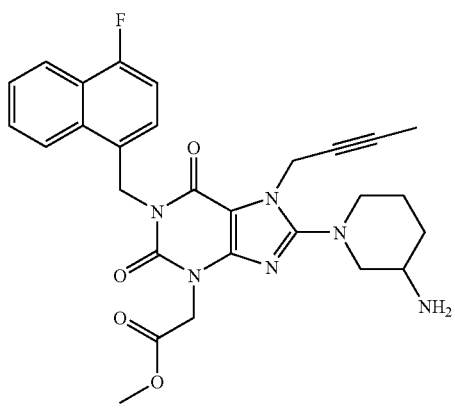 |
| (20) | 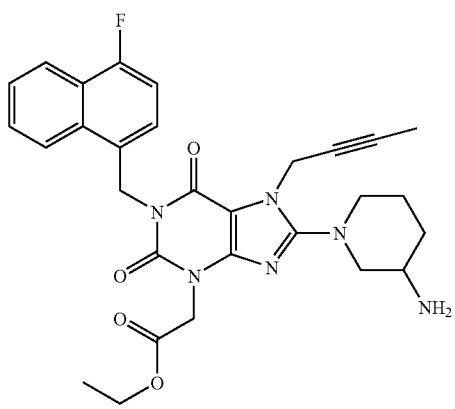 |
| Ex. | Structure |
|---|---|
| (21) | 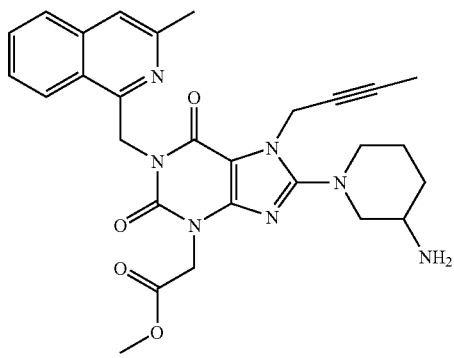 |
| (22) | 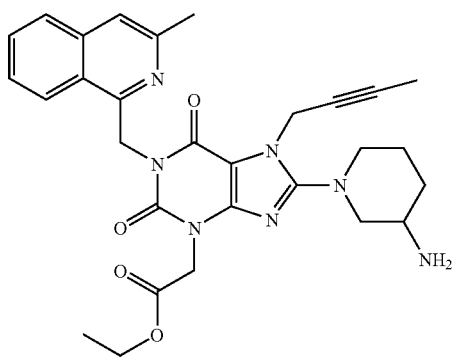 |
| (23) | 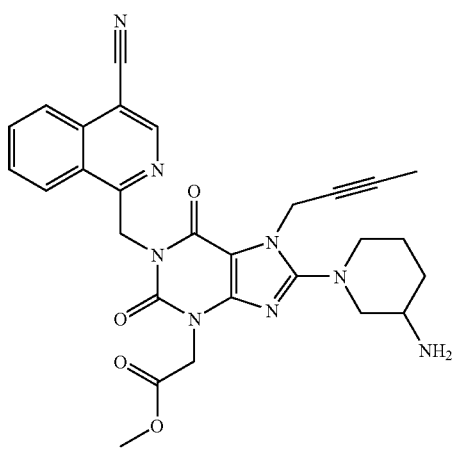 |

-continued
| Ex. | Structure |
|---|---|
| (24) | 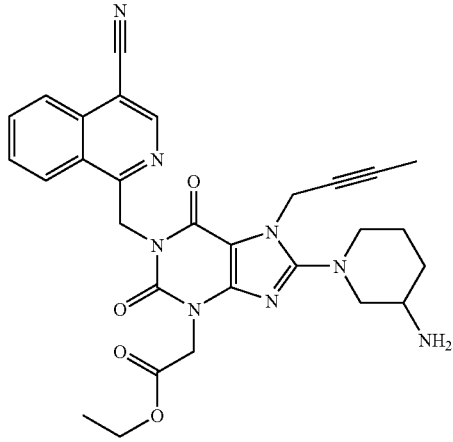 |
| (25) | 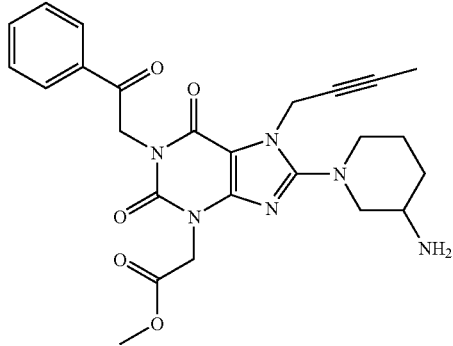 |
| (26) | 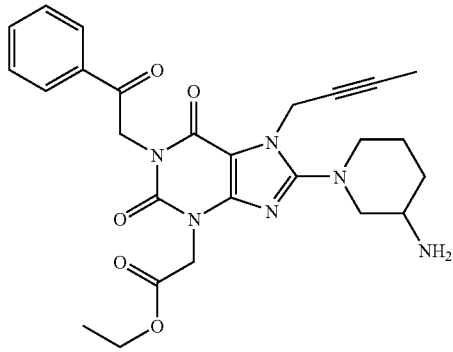 |
| (27) | 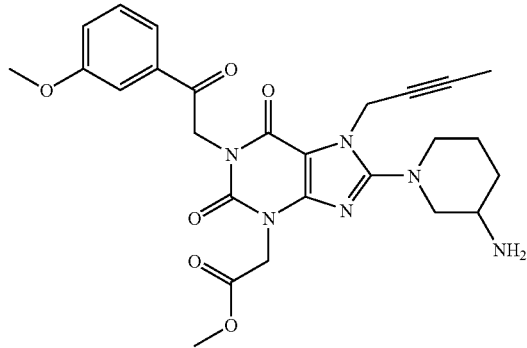 |
-continued
| Ex. | Structure |
|---|---|
| (28) | 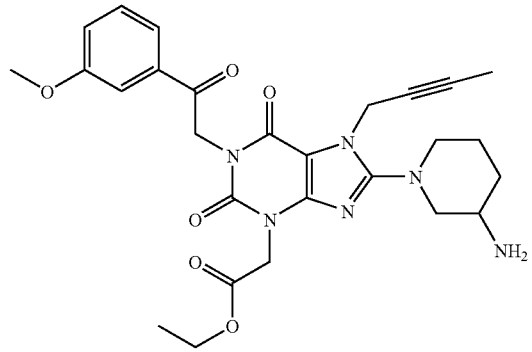 |
| (29) | 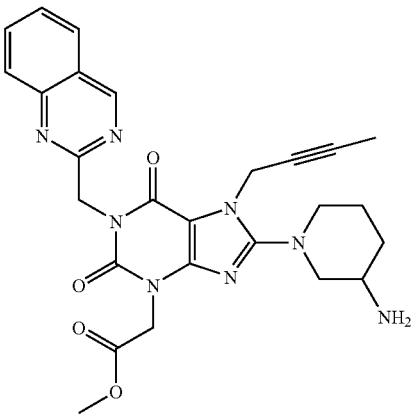 |
| (30) | 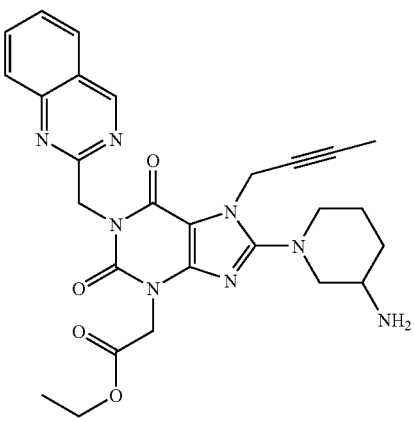 |

-continued
| Ex. | Structure |
|---|---|
| (31) | 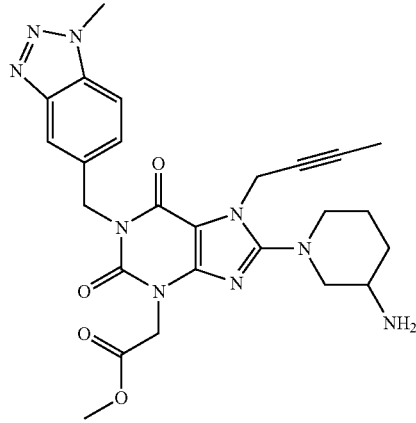 |
| (32) | 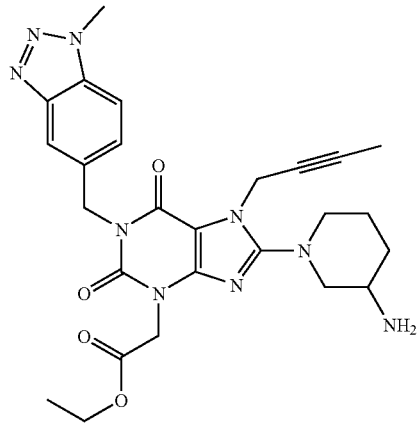 |
| (33) | 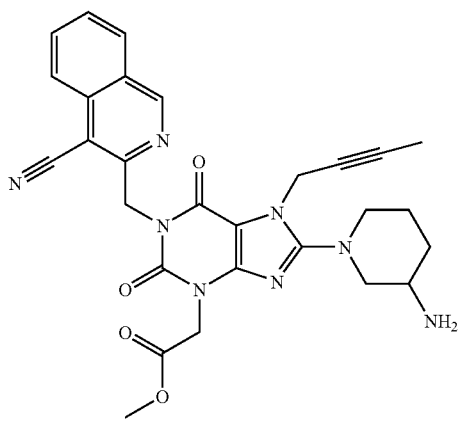 |
-continued
| Ex. | Structure |
|---|---|
| (34) | 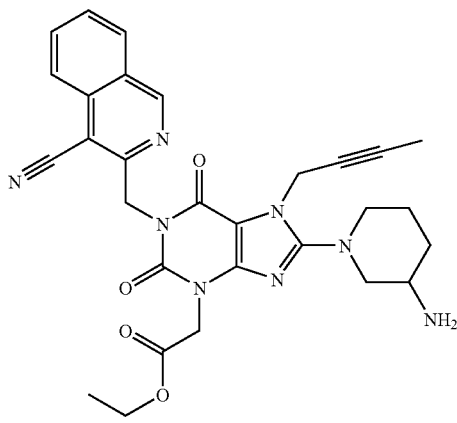 |
| (35) | 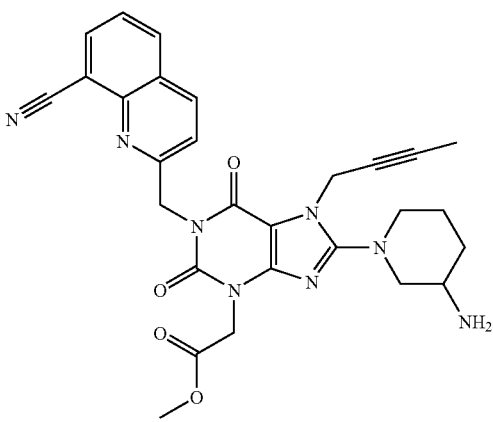 |
| (36) | 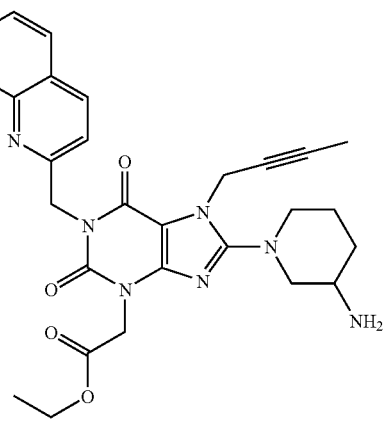 |

-continued
| Ex. | Structure |
|---|---|
| (37) | 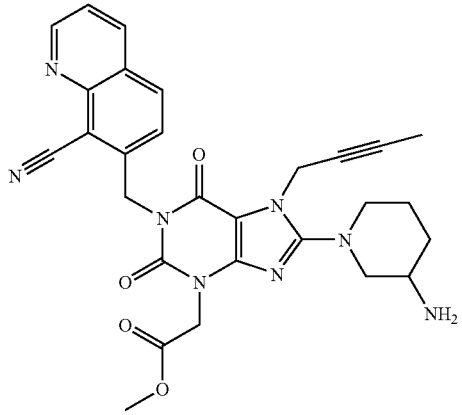 |
| (38) | 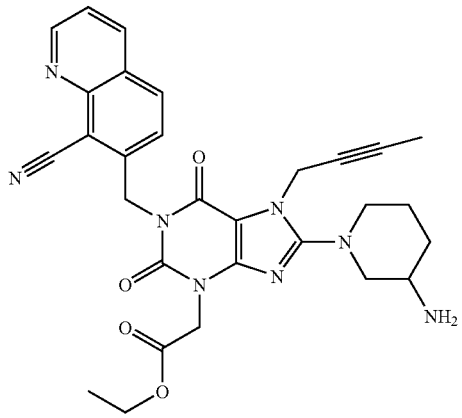 |
| (39) | 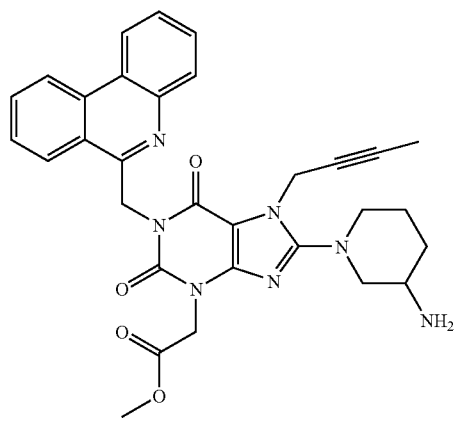 |
-continued
| Ex. | Structure |
|---|---|
| (40) | 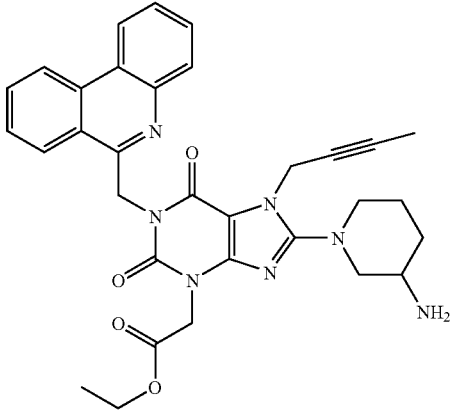 |
| (41) | 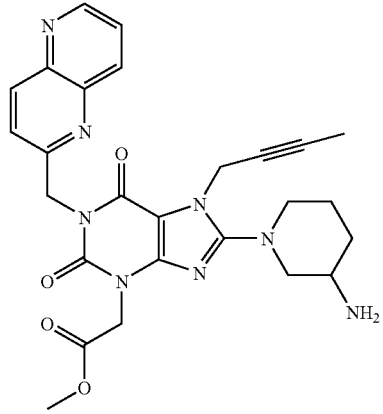 |
| (42) | 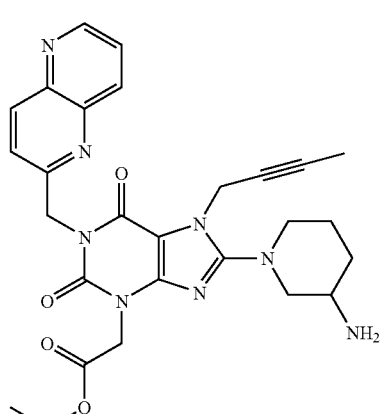 |

| Ex. | Structure |
|---|---|
| (43) | 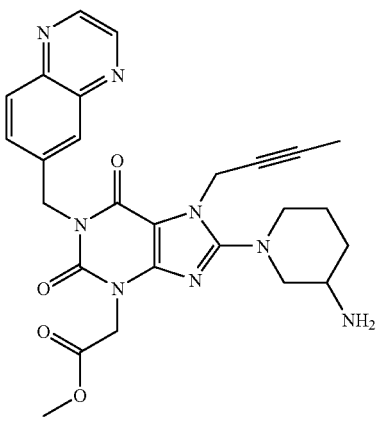 |
| (44) | 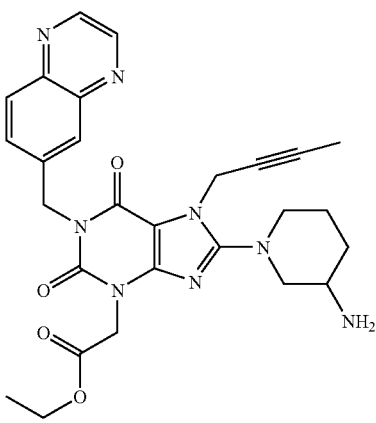 |
| (45) | 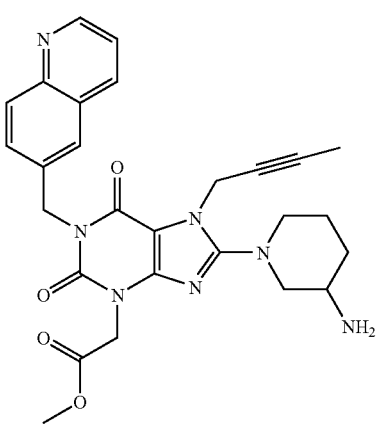 |
| Ex. | Structure |
|---|---|
| (46) | 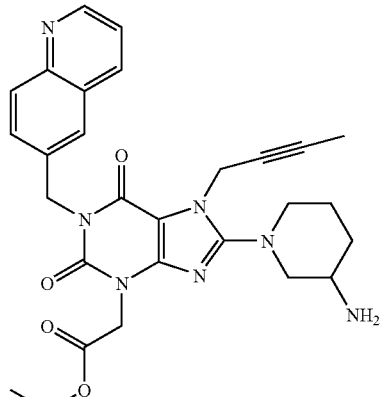 |
| (47) | 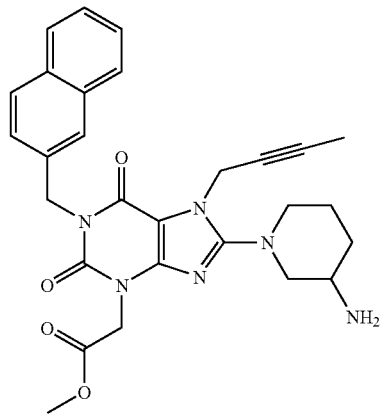 |
| (48) | 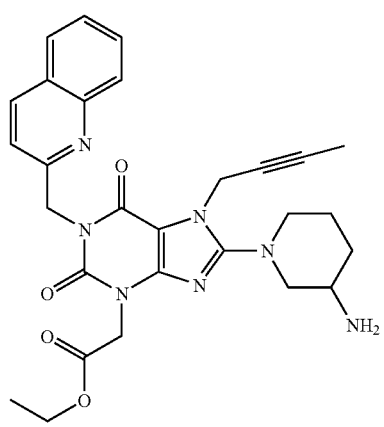 |

| Ex. | Structure | | Ex. | Structure |
|---|---|---|---|---|
| (49) | 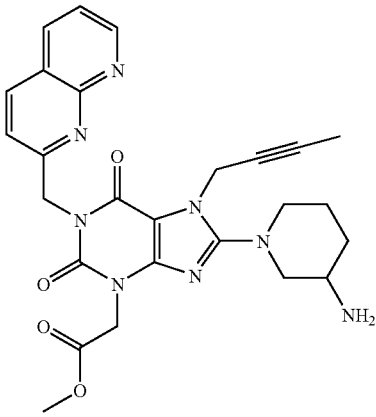 | | (52) | 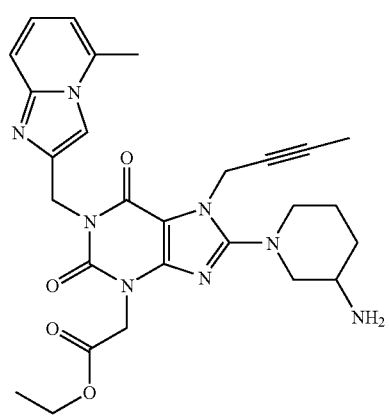 |
| (50) | 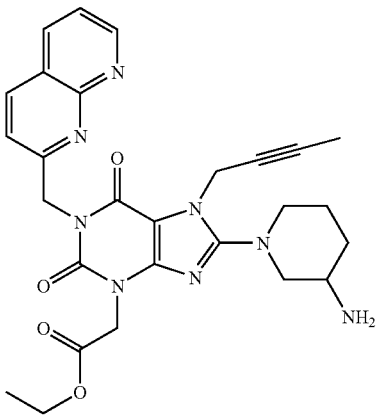 | | (53) | 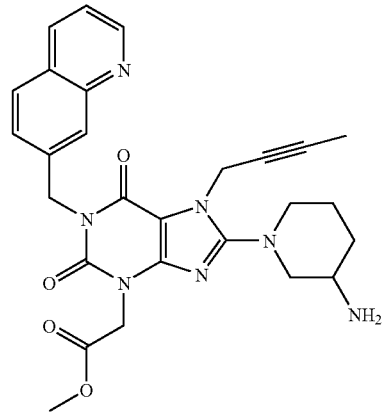 |
| (51) | 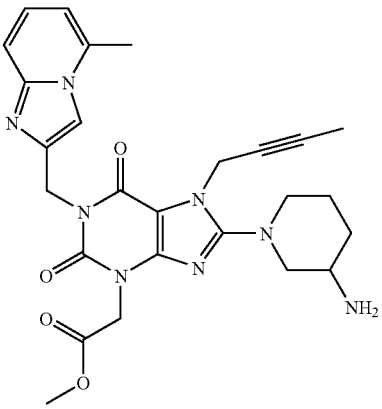 | | (54) | 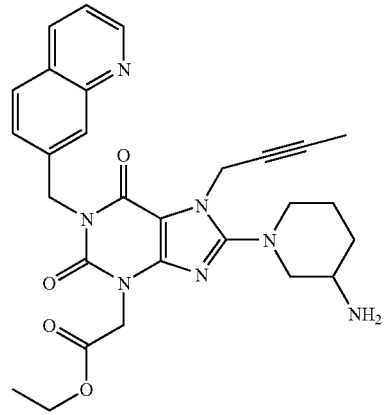 |

| Ex. | Structure |
|---|---|
| (55) | 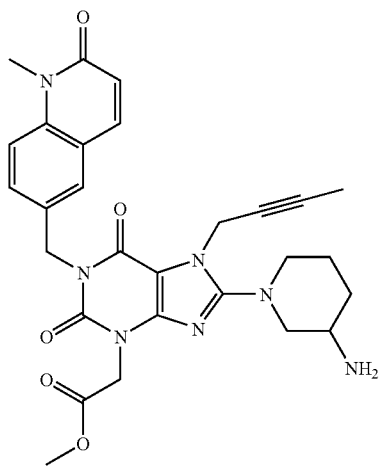 |
| (56) | 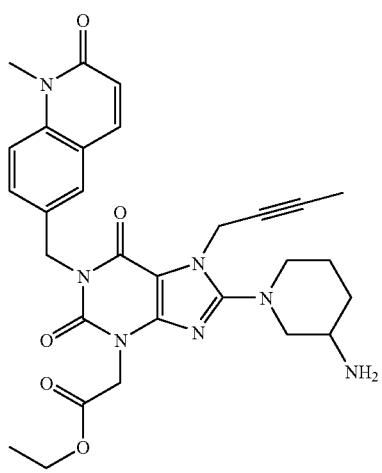 |
| (57) | 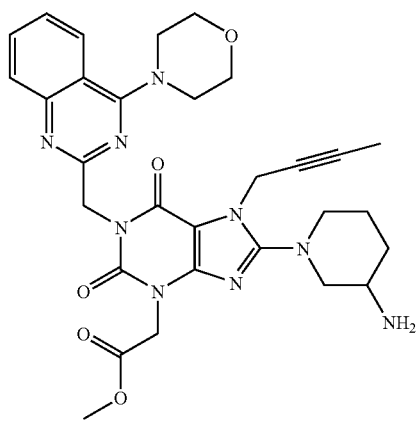 |
| (58) | 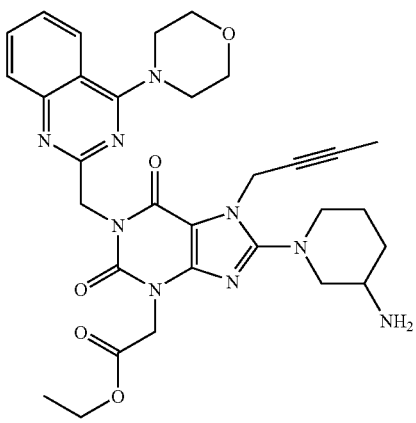 |
| (59) | 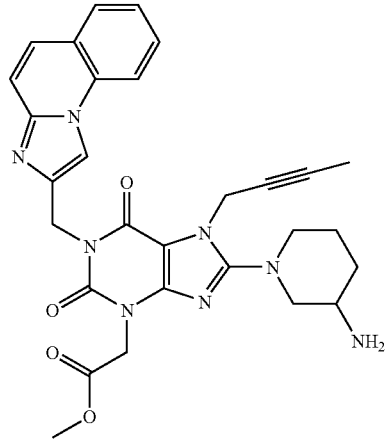 |
| (60) | 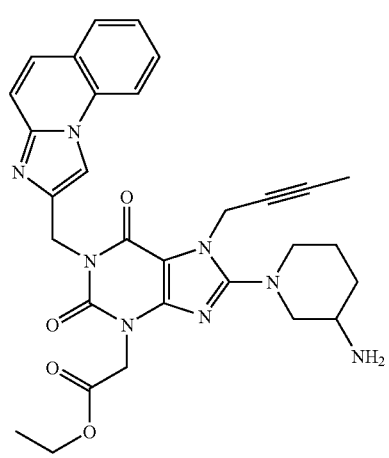 |

| Ex. | Structure |
|---|---|
| (61) | 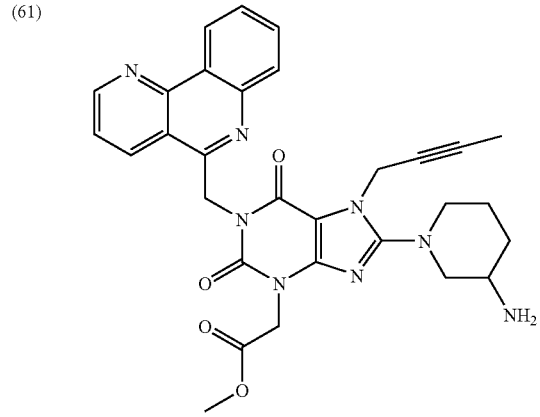 |
| (62) | 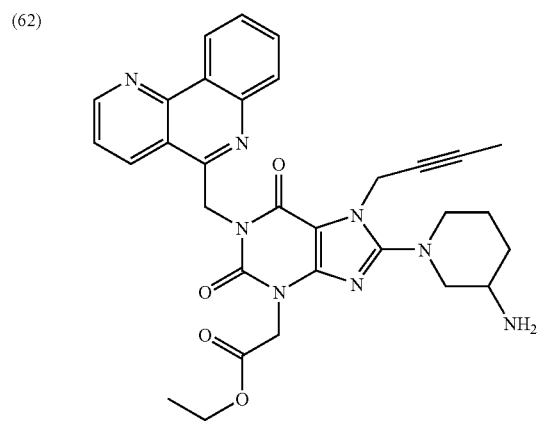 |
| (63) | 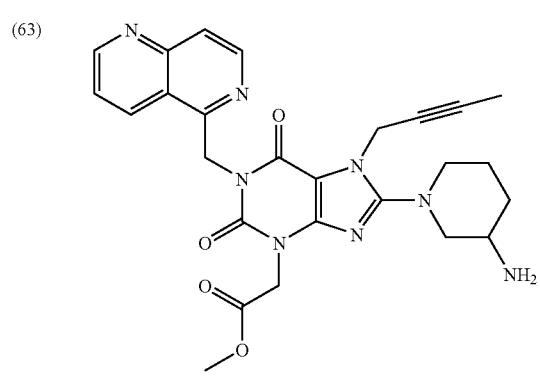 |
| (64) | 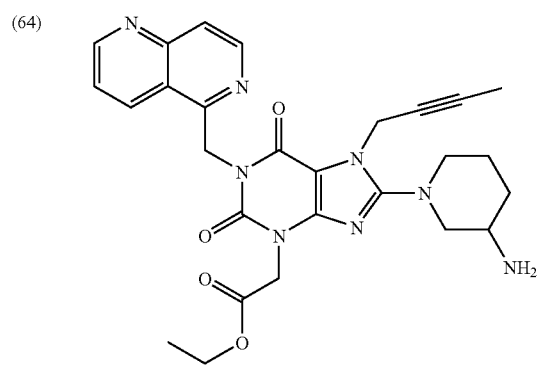 |
| Ex. | Structure |
|---|---|
| (65) | 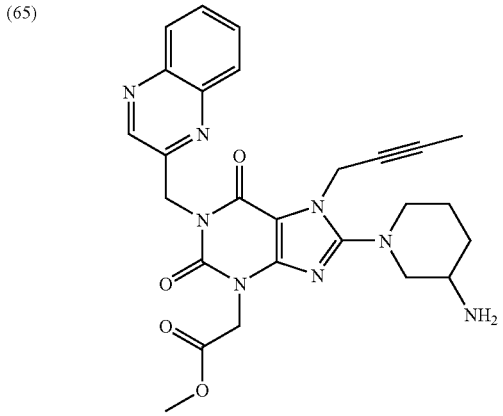 |
| (66) | 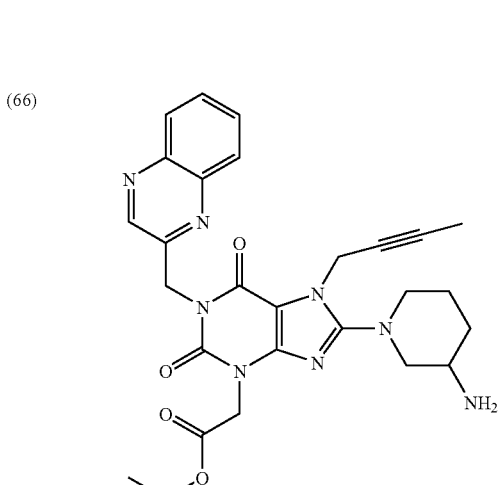 |
| (67) | |

-continued
| Ex. | Structure |
|---|---|
| (68) | 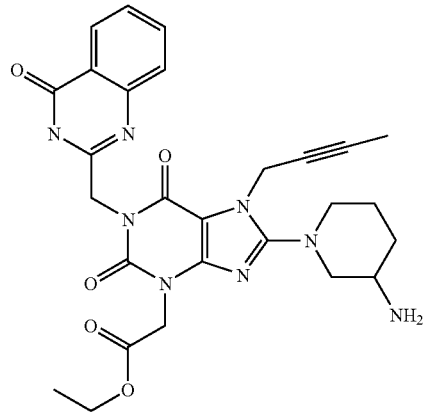 |
| (69) | 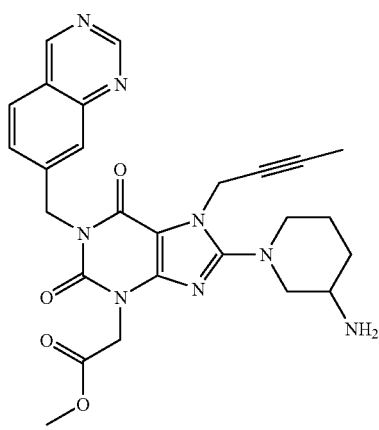 |
| (70) | 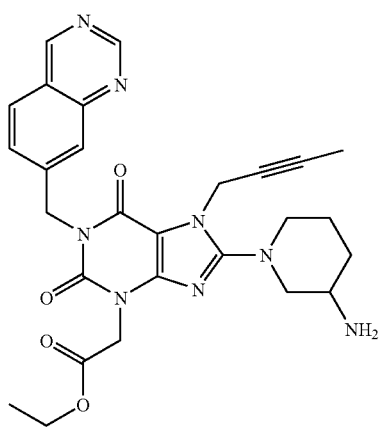 |
-continued
| Ex. | Structure |
|---|---|
| (71) | 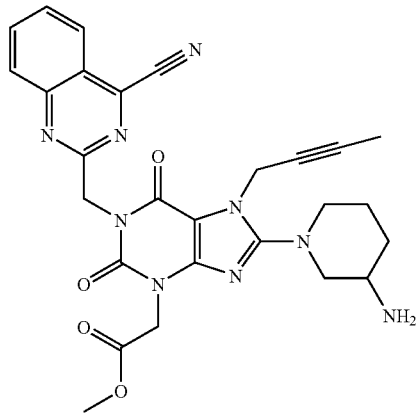 |
| (72) | 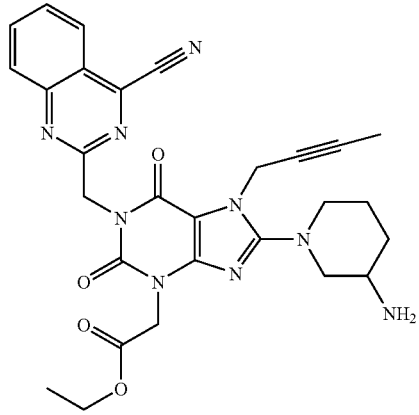 |
| (73) | 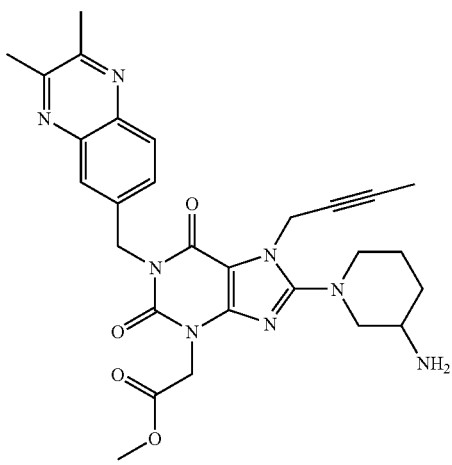 |

-continued
| Ex. | Structure |
|---|---|
| (74) | 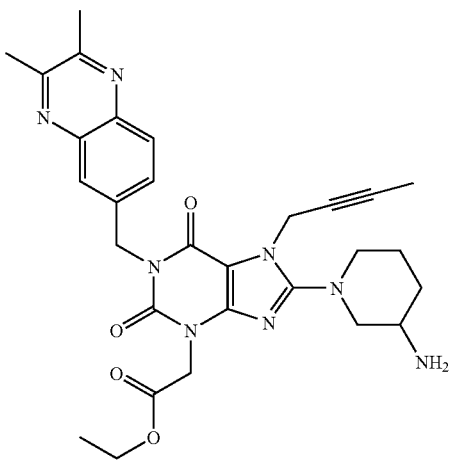 |
| (75) | 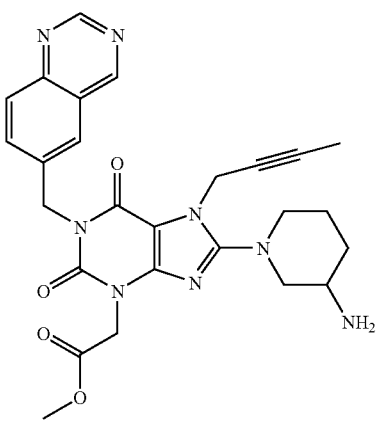 |
| (76) | 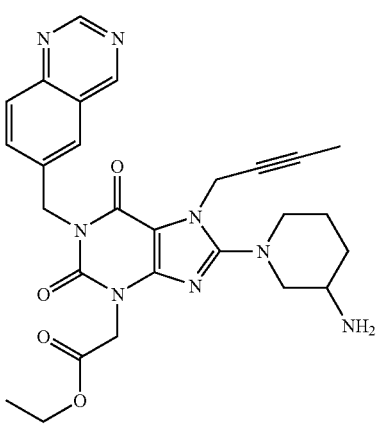 |
-continued
| Ex. | Structure |
|---|---|
| (77) | 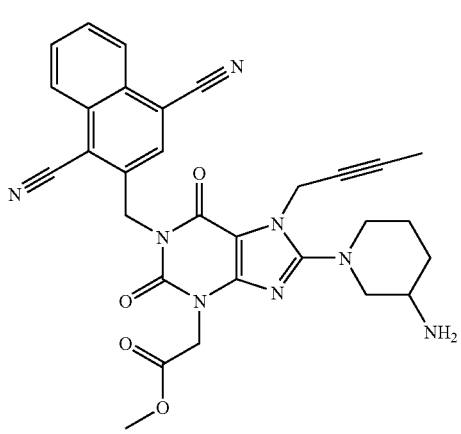 |
| (78) | 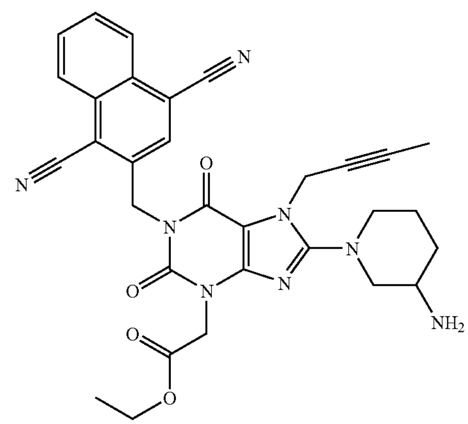 |
| (79) | 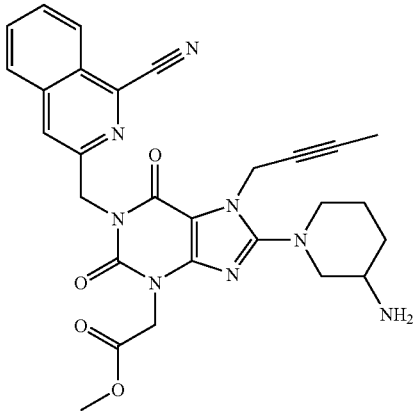 |

-continued
| Ex. | Structure |
|---|---|
| (80) | 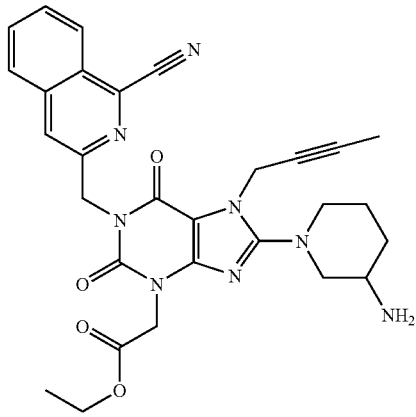 |
| (81) | 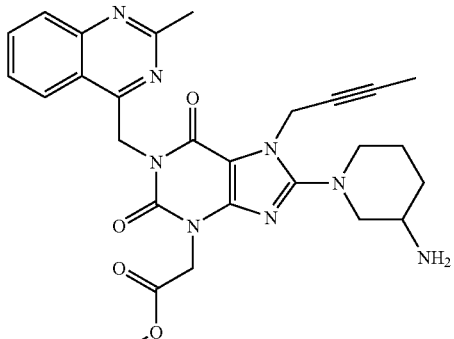 |
| (82) | 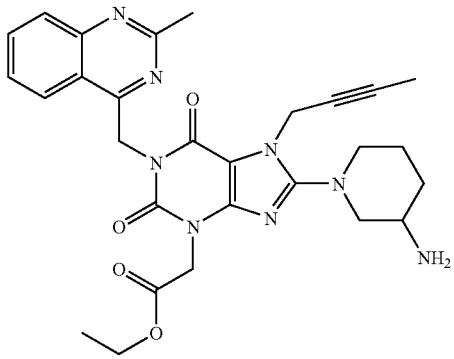 |
| (83) | 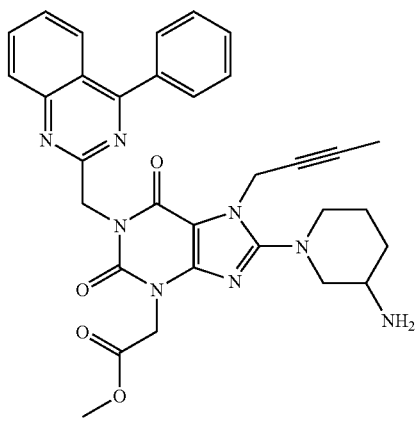 |
-continued
| Ex. | Structure |
|---|---|
| (84) | 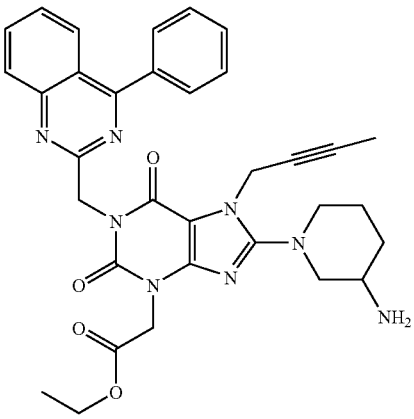 |
| (85) | 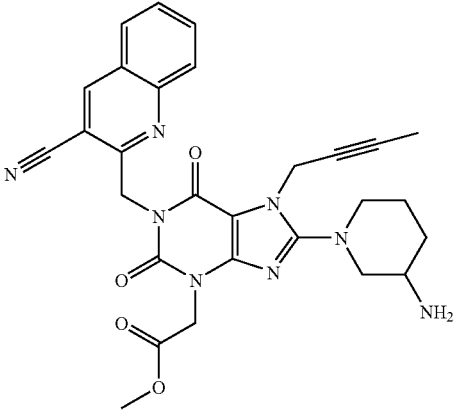 |
| (86) | 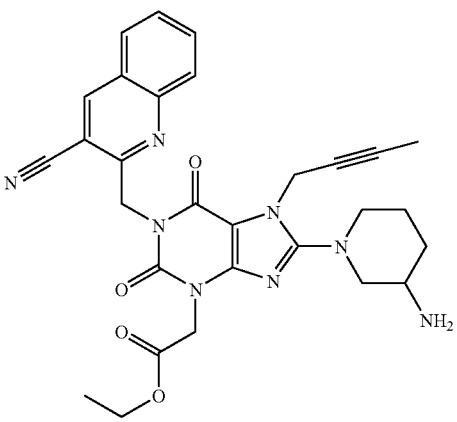 |

-continued
| Ex. | Structure |
|---|---|
| (87) | 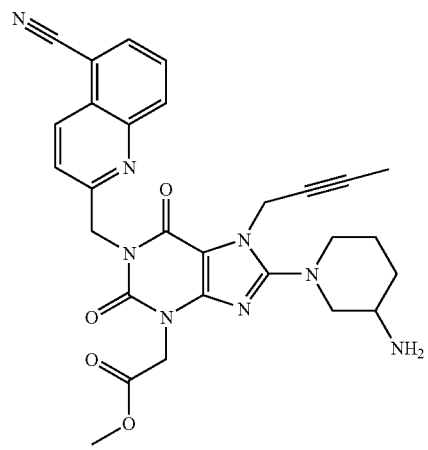 |
| (88) | 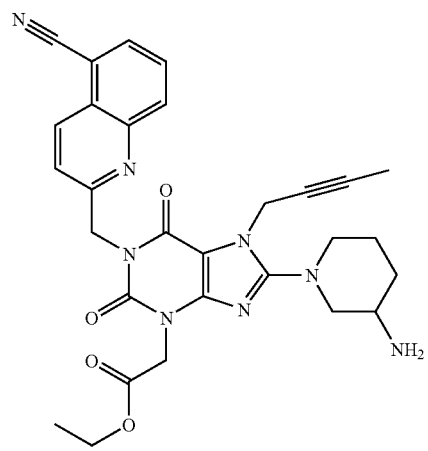 |
| (89) | 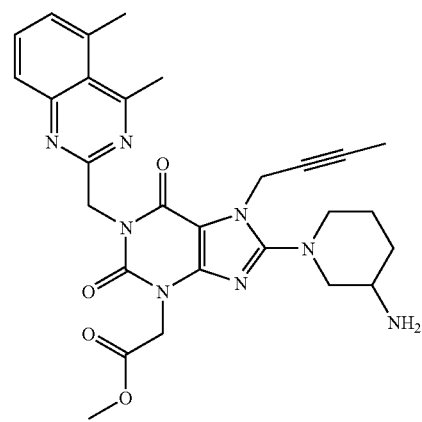 |
-continued
| Ex. | Structure |
|---|---|
| (90) | 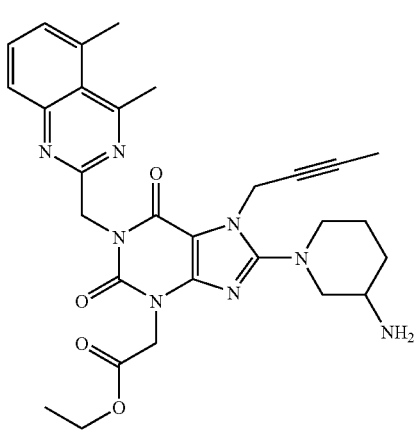 |
| (91) | 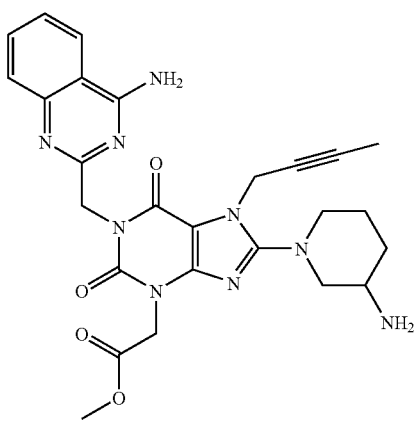 |
| (92) | 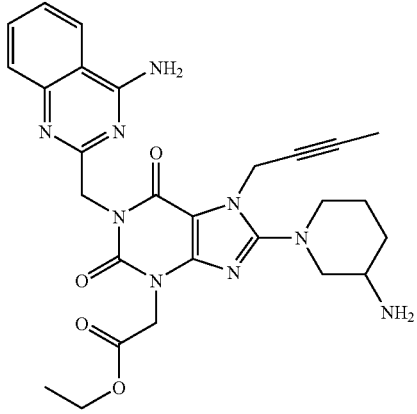 |

| Ex. | Structure |
|---|---|
| (93) | 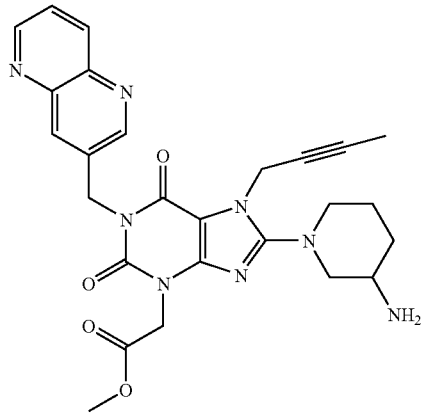 |
| (94) | 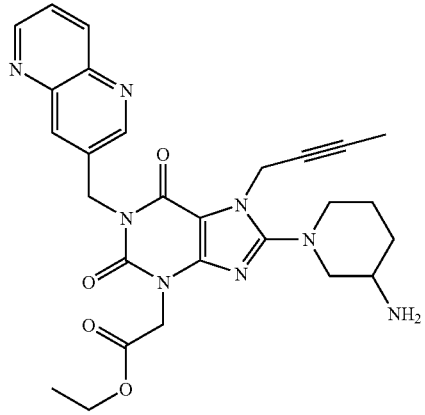 |
| (95) | 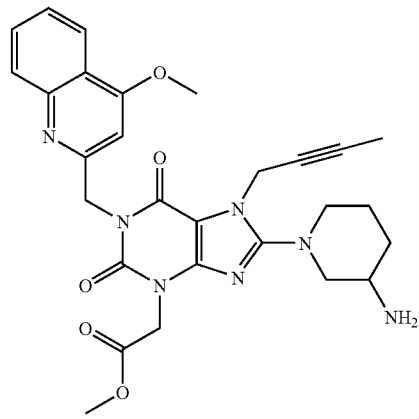 |
| Ex. | Structure |
|---|---|
| (96) | 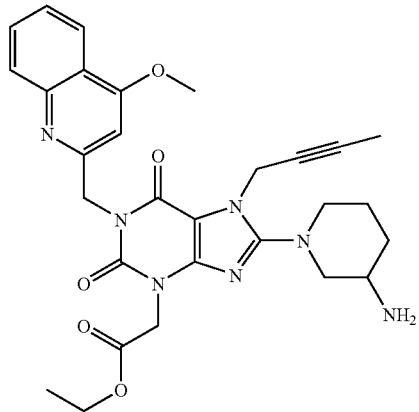 |
| (97) | 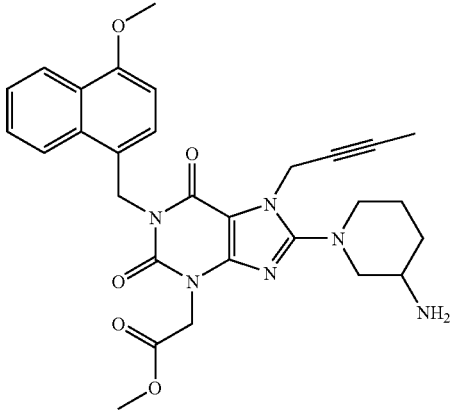 |
| (98) | 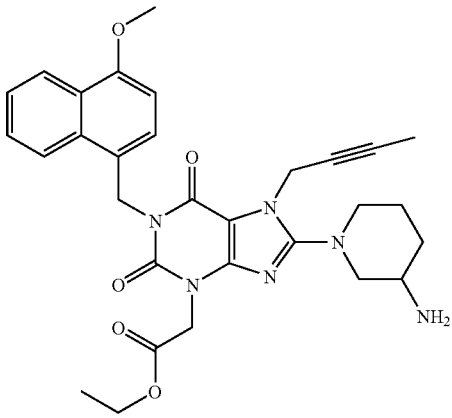 |

| Ex. | Structure |
|---|---|
| (99) | 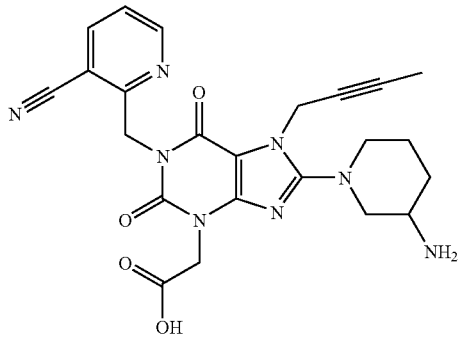 |
| (100) | 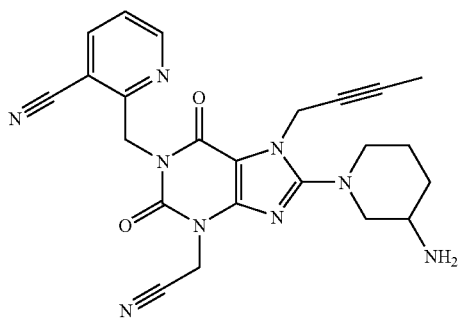 |
| (101) | 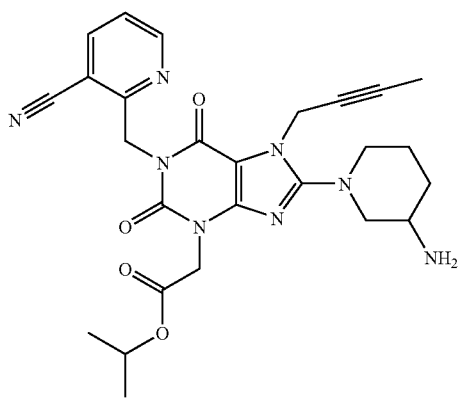 |
| (102) | 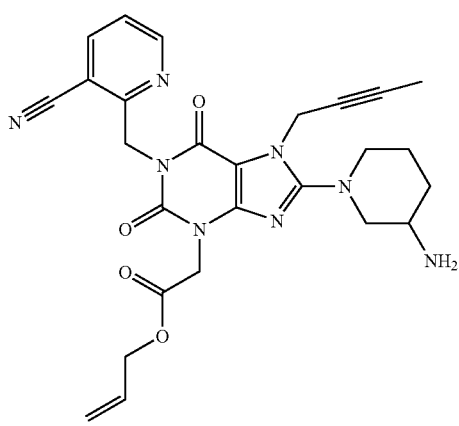 |
| Ex. | Structure |
|---|---|
| (103) | 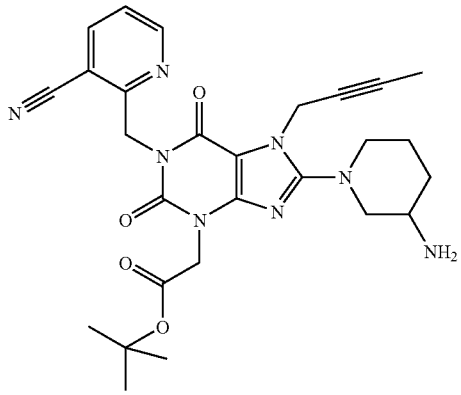 |
| (104) | 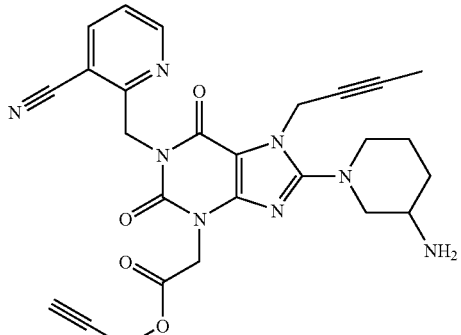 |
| (105) | 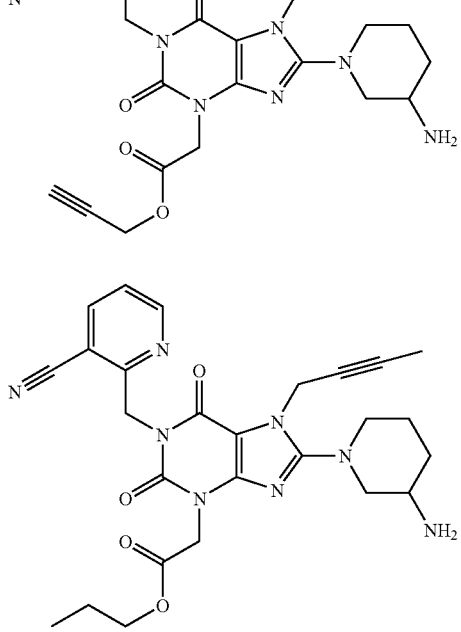 |
| (106) | 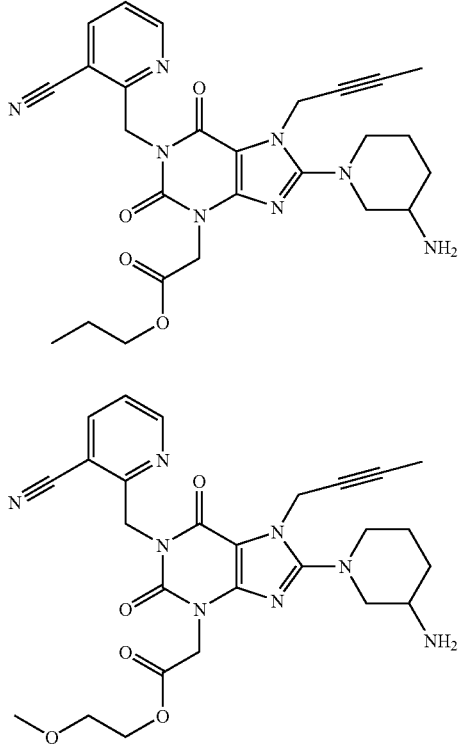 |

| Ex. | Structure |
|---|---|
| (107) | 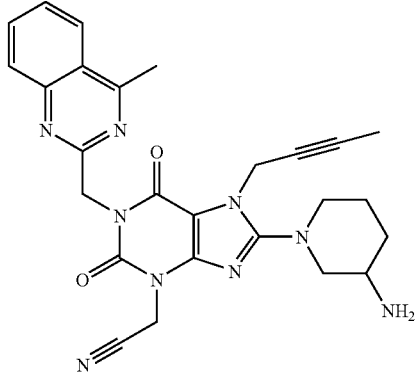 |
| (108) | 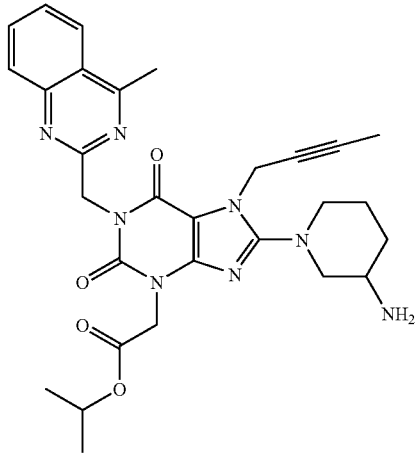 |
| (109) | 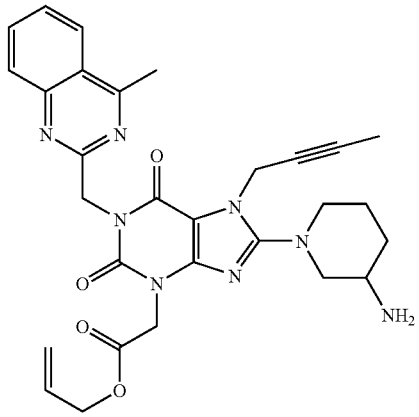 |
| (110) | 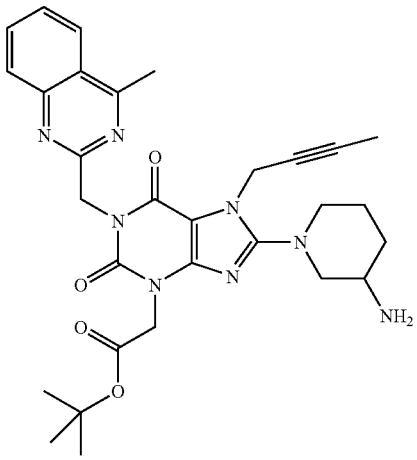 |
| (111) | 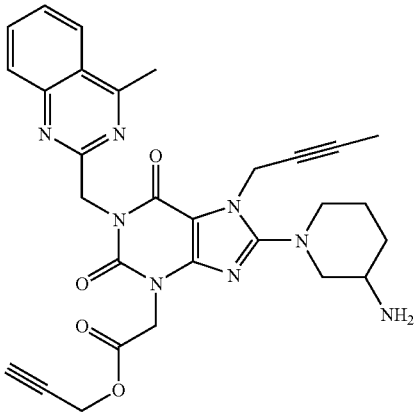 |
| (112) | 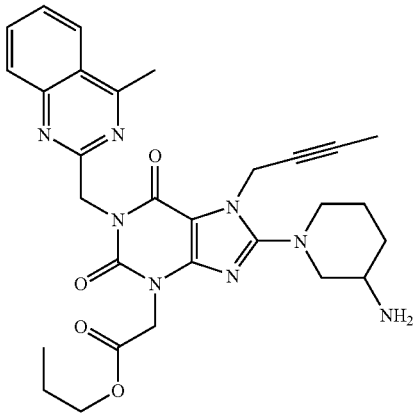 |

| Ex. | Structure |
|---|---|
| (113) | 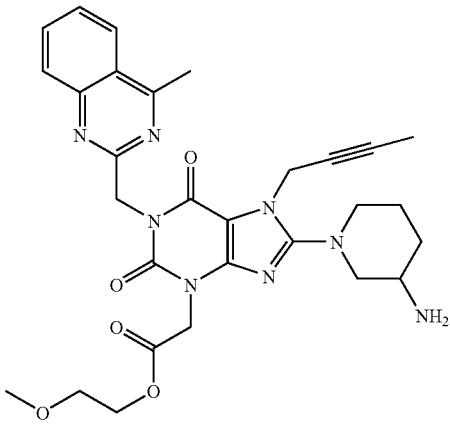 |
| (114) | 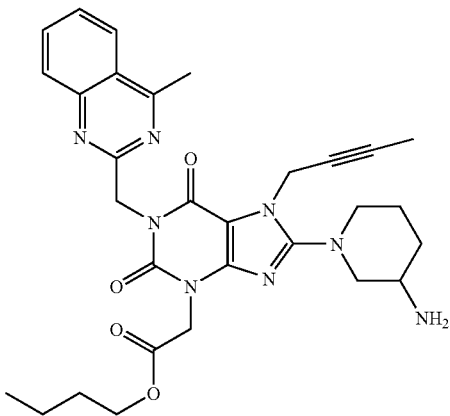 |
| (115) | 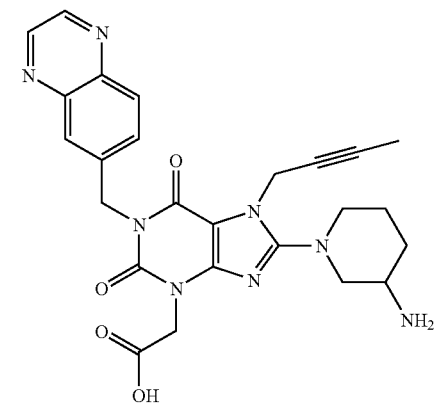 |
| Ex. | Structure |
|---|---|
| (116) | 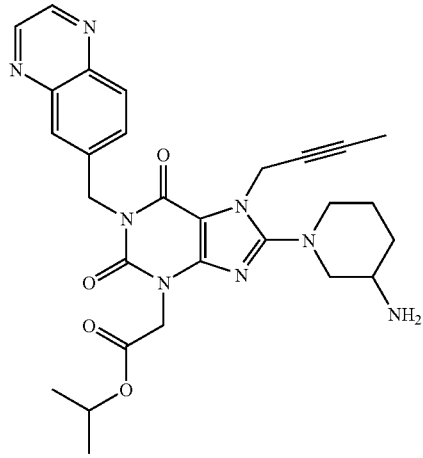 |
| (117) | 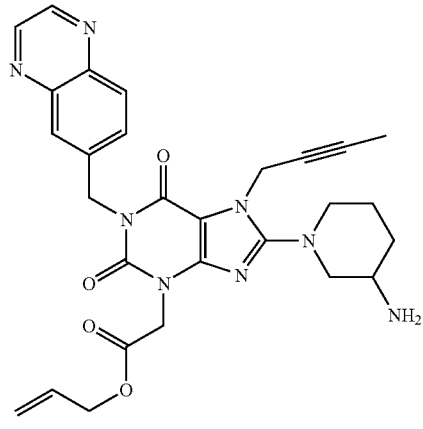 |
| (118) | 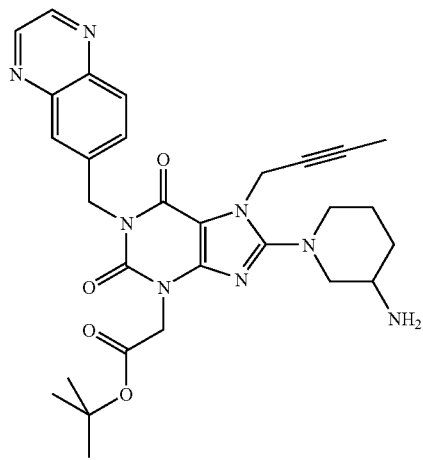 |

| Ex. | Structure |
|---|---|
| (119) | 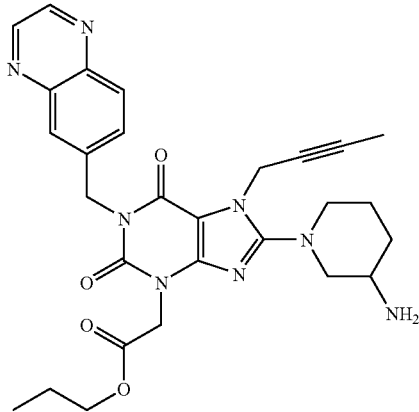 |
| (120) | 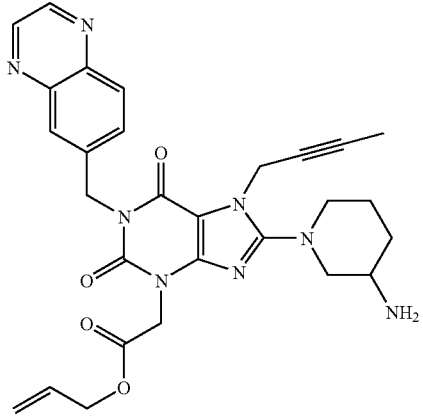 |
| (121) | 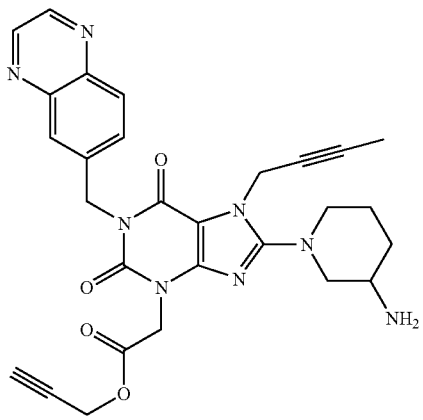 |
| Ex. | Structure |
|---|---|
| (122) | 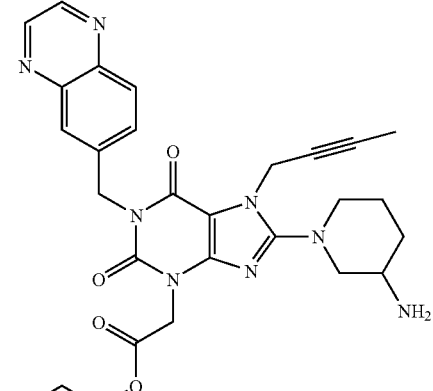 |
| (123) | 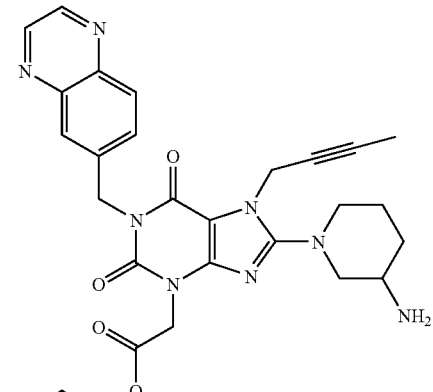 |
| (124) | 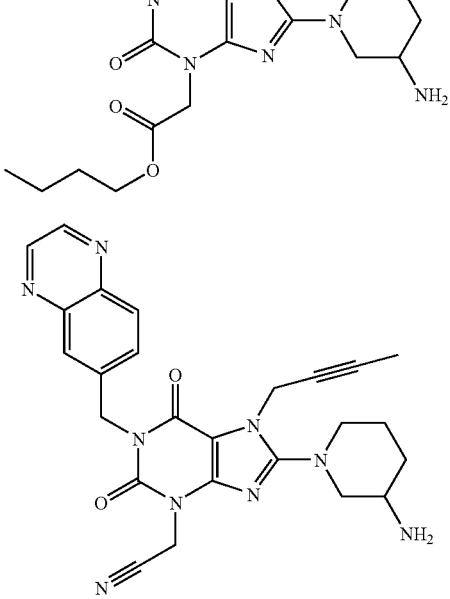 |
| (125) | 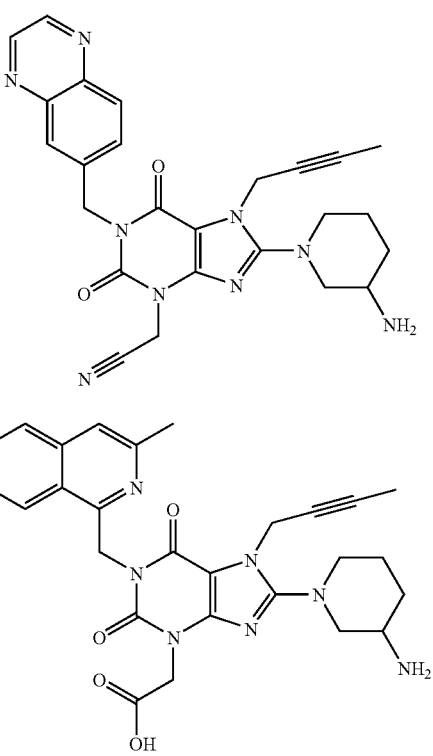 |

-continued

| Ex. | Structure |
|---|---|
| (126) | 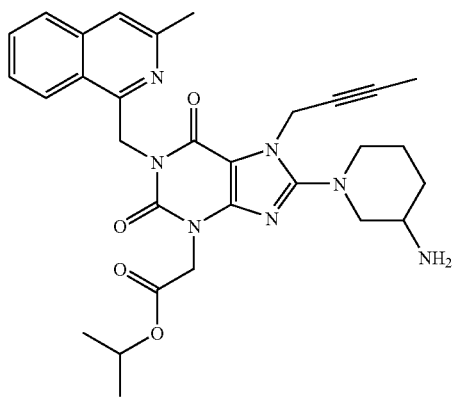 |
| (127) | 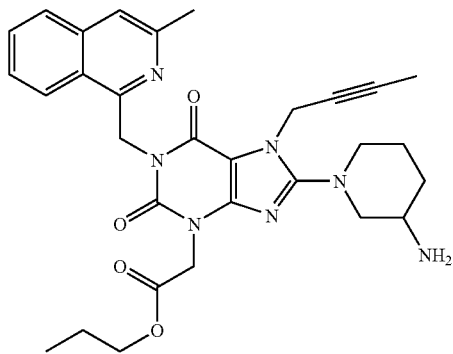 |
| (128) | 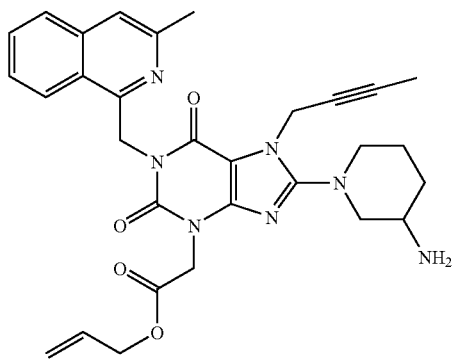 |
| (129) | 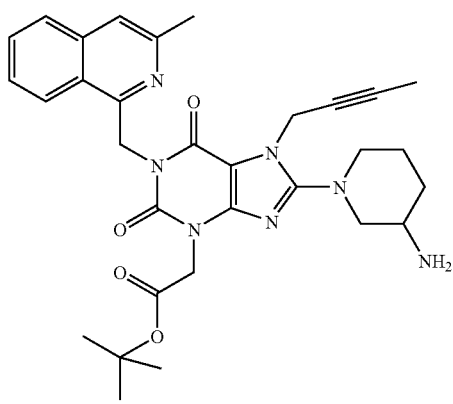 |

-continued

| Ex. | Structure |
|---|---|
| (130) | 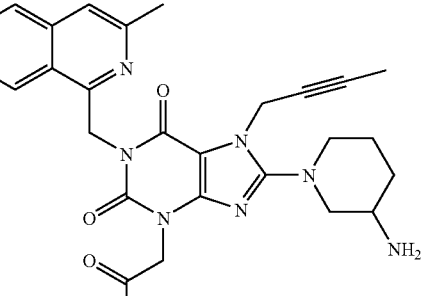 |
| (131) | 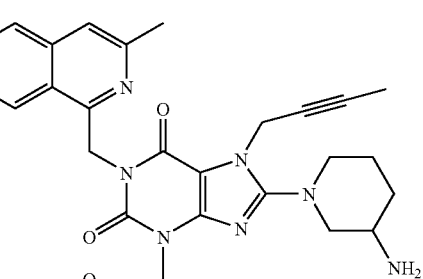 |
| (132) | 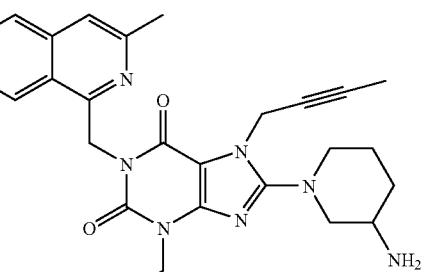 |

EXAMPLE 3

Coated Tablets Containing 75 mg of Active Substance 1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinyl pyrrolidone, hydroxypropylmethylcellulose and half the specified amount of magnesium stearate.

Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 4

Tablets Containing 100 mg of Active Substance
Composition:

1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE 5

Tablets Containing 150 mg of Active Substance
Composition:

1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm.

The granules, dried at 45° C., are passed through the same screen again and mixed with the specified amount of magnesium stearate. Tablets are pressed from the mixture.

Weight of tablet: 300 mg
die: 10 mm, flat

EXAMPLE 6

Hard Gelatine Capsules Containing 150 mg of Active Substance 1 capsule contains:

| | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 7

Suppositories Containing 150 mg of Active Substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 8

Suspension Containing 50 mg of Active Substance 100 ml of suspension contain:

| | | |
|---|---|---|
| active substance | 1.00 | g |
| carboxymethylcellulose-Na-salt | 0.10 | g |
| methyl p-hydroxybenzoate | 0.05 | g |
| propyl p-hydroxybenzoate | 0.01 | g |
| glucose | 10.00 | g |
| glycerol | 5.00 | g |
| 70% sorbitol solution | 20.00 | g |
| flavouring | 0.30 | g |
| dist. water | ad 100 | ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 9

Ampoules Containing 10 mg Active Substance

Composition:

| active substance | 10.0 mg |
|---|---|
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 10

Ampoules Containing 50 mg of Active Substance

Composition:

| active substance | 50.0 mg |
|---|---|
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

What is claimed is:

1. A compound of formula (I):

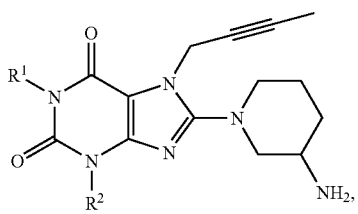

wherein
$R^1$ denotes a phenylmethyl, phenylprop-2-enyl, pyridinylmethyl, pyrimidinylmethyl, naphthylmethyl, quinolinylmethyl, 1H-quinolin-2-onyl-methyl, imidazo[1,2-a]quinolinylmethyl, quinazolinylmethyl, 3H-quinazolin-4-onylmethyl, quinoxalinylmethyl, phenanthridinylmethyl, naphthyridinyl-methyl, benzo[1.6]naphthyridinylmethyl, imidazopyridinylmethyl or benzotriazolyl-methyl group which may be substituted in each case by one or two fluorine, chlorine or bromine atoms or one or two cyano, nitro, amino, $C_{1-3}$-alkyl, $C_{1-3}$-alkyloxy, phenyl or morpholinyl groups, while the substituents may be identical or different, $R_2$ denotes a cyano-$C_{1-3}$-alkyl, hydroxycarbonylmethyl, $C_{1-6}$-alkyloxycarbonylmethyl, $C_{3-6}$-alkenyloxycarbonylmethyl, $C_{3-6}$-cycloalkyl-$C_{1-3}$-alkyloxycarbonylmethyl or $C_{3-6}$-cycloalkyloxycarbonylmethyl group, while the alkyl, alkenyl and cycloalkyl groups in each case may be substituted by one or two $C_{1-3}$-alkyl or $C_{1-3}$-alkyloxy groups and/or partly or completely fluorinated, while, unless otherwise stated, the above-mentioned alkyl, alkenyl and alkynyl groups may be straight-chain or branched, or a tautomer, enantiomer, diastereomer, or a mixture thereof, a prodrug thereof or a salt thereof.

2. The compound according to claim 1, wherein
$R^1$ denotes a pyridinylmethyl, pyrimidinylmethyl, quinazolinyl-methyl, quinoxalinylmethyl or naphthyl-methyl group which may be substituted by one or two cyano or methyl groups, and
$R^2$ denotes a cyanomethyl, hydroxycarbonylmethyl, methoxycarbonylmethyl or ethoxycarbonylmethyl group.

3. The compound according to claim 1, wherein
$R^1$ denotes a quinazolinylmethyl group which may be substituted by a methyl group, and
$R^2$ denotes a methyl group substituted by a $C_{1-4}$-alkoxycarbonyl group.

4. A compound selected from:
(a) 1-(naphthyl-1-ylmethyl)-3-(methoxycarbonylmethyl)-7-(but-2-ynyl)-8-(3-amino-piperidin-1-yl)-xanthine
(b) 1-(naphthyl-1-ylmethyl)-3-(cyanomethyl)-7-(but-2-ynyl)-8-(3-amino-piperidin-1-yl)-xanthine
(c) (R)-1-(4-methyl-quinazolin-2-ylmethyl)-3-(methoxycarbonylmethyl)-7-(but-2-ynyl)-8-(3-amino-piperidin-1-yl)-xanthine
(d) (R)-1-(4-methyl-quinazolin-2-ylmethyl)-3-(ethoxycarbonylmethyl)-7-(but-2-ynyl)-8-(3-amino-piperidin-1-yl)-xanthine
(e) (R)-1-(4-methyl-quinazolin-2-ylmethyl)-3-(hydroxycarbonylmethyl)-7-(but-2-ynyl)-8-(3-amino-piperidin-1-yl)-xanthine or
a tautomer or a salt thereof.

5. A physiologically acceptable salt of a compound according to claim 1 with an inorganic or organic acid or base.

6. A pharmaceutical composition, comprising a pharmaceutically acceptable amount of a compound according to claim 1 together with one or more inert carriers or diluents.

7. A method of treating type II diabetes mellitus or obesity comprising administering to a patient in need thereof a therapeutically effective amount of a compound according to claim 1.

8. A method of treating type II diabetes mellitus comprising administering to a patient in need thereof a therapeutically effective amount of a compound according to claim 1.

9. A method of treating obesity comprising administering to a patient in need thereof a therapeutically effective amount of a compound according to claim 1.

10. The method of claim 7, wherein the compound is administered to the patient by intravenous route in an amount of 1 to 100 mg or by oral route in an amount of 1 to 1000 mg, in each case 1 to 4 times a day.

11. The method of claim 7, wherein the compound is administered to the patient by intravenous route in an amount of 1 to 30 mg, or by oral route in an amount of 1 to 100 mg, in each case 1 to 4 times a day.

12. A compound according to claim 1, wherein:

$R^1$ denotes a phenylmethyl, phenylprop-2-enyl, pyridinylmethyl, pyrimidinylmethyl, imidazo [1,2-a]quinolinylmethyl, quinoxalinylmethyl, phenanthridinylmethyl, naphthyridinyl-methyl, benzo [1.6]naphthyridinylmethyl, imidazopyridinylmethyl or benzotriazolyl-methyl group which may be substituted in each case by one or two fluorine, chlorine or bromine atoms or one or two cyano, nitro, amino, $C_{1-3}$-alkyl, $C_{1-3}$-alkyloxy, phenyl or morpholinyl groups, while the substituents may be identical or different.

13. A compound according to claim 1, wherein:

$R^2$ denotes a hydroxycarbonylmethyl, ethoxycarbonylmethyl, $C_{3-6}$-alkenyloxycarbonylmethyl, $C_{3-6}$-cycloalkyl-$C_{1-3}$-alkyloxycarbonylmethyl or $C_{3-6}$-cycloalkyloxycarbonylmethyl group, while the alkyl, alkenyl and cycloalkyl groups in each case may be substituted by one or two $C_{1-3}$-alkyl or $C_{1-3}$-alkyloxy groups and/or partly or completely fluorinated.

\* \* \* \* \*